United States Patent [19]

Bohme et al.

[11] Patent Number: 4,730,006

[45] Date of Patent: Mar. 8, 1988

[54] DERIVATIVES OF 2,6-DIAMINO-3-HALOHEPTANEDIOIC ACID

[75] Inventors: Ekkehard H. Bohme, Cincinnati, Ohio; Fritz Gerhart, Kehl Leutesheim, Fed. Rep. of Germany; William Higgins, Strasbourg, France

[73] Assignee: Merrell Dow Pharmaceuticals Inc., Cincinnati, Ohio

[21] Appl. No.: 822,436

[22] Filed: Jan. 27, 1986

[51] Int. Cl.$^4$ .................. A61K 31/195; A61K 31/24; C07C 101/26; C07K 5/06; C07K 5/08; C07K 5/10

[52] U.S. Cl. .................................. 514/538; 560/169; 562/566; 514/561; 514/540; 514/18; 514/19; 530/330; 530/331

[58] Field of Search ................. 514/538, 561, 540, 18, 514/19; 530/330, 331; 560/16.9; 562/56.6

[56] References Cited

PUBLICATIONS

D. Schott, et al., Journal of Labelled Compounds & Radiopharmaceuticals, vol. XXII; No. 2 (1984), pp. 127–133.

*Primary Examiner*—Delbert R. Phillips
*Attorney, Agent, or Firm*—Stephen L. Nesbitt

[57] ABSTRACT

This invention relates to amino acid, dipeptide and tripeptide derivatives of 2,6-diamino-3-haloheptanedioic acids, processes for preparing the same, and their use as antibacterial agents.

16 Claims, No Drawings

DERIVATIVES OF 2,6-DIAMINO-3-HALOHEPTANEDIOIC ACID

BACKGROUND AND DESCRIPTION 2,6-diaminopimelic acid, or 2,6-diaminoheptanedioic acid, is a normal constituent of bacterial cell walls that plays an important role in cell wall rigidity. Bacterial cell wall rigidity is thought to be maintained by virtue of peptide crosslinking bonds between diaminopimelic acid and D-alanine moieties. This function of diaminopimelic acid appears to be necessary in all gram negative bacteria and also for some members of the genus Bacillus. More particularly, the DL isomer of diaminopimelic acid appears to be involved in bacterial cell wall synthesis. That is to say, the asymmetric carbon atom adjacent to one of the carboxyl groups is in the D-configuration, whereas the asymmetric carbon atom adjacent to the remaining carboxyl group is in the L-configuration.

The metabolic synthesis of D,L-diaminopimelic acid occurs via the lysine biosynthetic pathway. The penultimate step in this pathway involves the epimerization of the L,L-isomer of diaminopimelic acid to the corresponding D,L-isomer utilizing the enzyme 2,6-L,L-diaminopimelate-2-epimerase (DAP-epimerase). Thus, in principle, any inhibitor of the enzyme DAP-epimerase should prevent the formation of D,L-diaminopimelic acid with a concomitant inhibition of bacterial cell growth.

SUMMARY OF THE INVENTION

This invention relates to a class of amino acid or peptide derivatives of 2,6-diamino-3-halo-heptanedioic acid. More particularly, this invention relates to a class of 2,6-diamino-3-halo-heptanedioic acid derivatives having the formula:

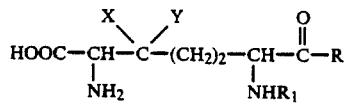

wherein:
R is hydroxy, $(C_1-C_4)$alkoxy or an amino acid, dipeptide or tripeptide residue;
$R_1$ is hydrogen or an amino acid, dipeptide or tripeptide residue, with the proviso that when $R_1$ is an amino acid, dipeptide or tripeptide residue then R must be hydroxy, and with the further proviso that when R is an amino acid, dipeptide or tripeptide residue then $R_1$ must be hydrogen;
X and Y are independently hydrogen, fluorine or chlorine, with the proviso that X and Y cannot both be hydrogen; and the pharmaceutically acceptable salts or optical isomers thereof.

Still more particularly, this invention relates to such compounds, compositions containing the same and their use as antibacterial agents.

DETAILED DESCRIPTION OF THE INVENTION

As can be seen from general formula (1) above, all of the compounds of this invention can be regarded as halogenated derivatives of 2,6-diaminopimelic acid. In order to be consistent with the nomenclature employed, the compounds described herein will neither be designated via their trivial name, i.e., as derivatives of pimelic acid, nor be designated by their more specific chemical names, i.e., as derivatives of 2,6-diamino-3-halo-heptanedioic acid, but as derivatives of ε-carboxylysine to facilitate the discrimination between the two carboxyls and the two amino functions. As indicated in formula (1) above, all of the compounds described are δ-halogenated derivatives of ε-carboxylysine, i.e., with the halogen in a beta position to the free terminal carboxyl group of the molecule.

The symbol R can represent the hydroxyl group in which case the compounds represent the δ-halo-ε-carboxylysines themselves. Alternatively, when R represents $(C_1-C_4)$alkoxy, the simple mono-esters of said δ-halo-ε-carboxylysines are defined. The term "alkoxy" is intended to refer to the lower alkyl groups such as: methoxy, ethoxy, n-propoxy, isopropoxy, n-butoxy, isobutoxy and t-butoxy.

When the symbol R represents an amino acid, a dipeptide or tripeptide residue, it is intended that a simple amide or a peptide bond is created at the carbonyl function in combination with the amino moiety of the particular amino acid(s) being utilized.

The amino acids contemplated within the scope of this invention include glycine and the L-isomers of alanine, methionine, valine, leucine and isoleucine. The simple amides, monopeptides or dipeptides that are formed are highly effective for the transport of the active δ-halo-ε-carboxylysine derivatives through the bacterial cell wall to their site of action.

The compounds of formula (1) have two chiral centers associated with the amine bearing carbon atoms and can occur as optically active forms, i.e., as optical isomers associated with the amine nitrogen bearing carbon atoms. These isomers are conventionally designated by the symbols L and D, S and R or combinations thereof. All of the amino acid, dipeptide or tripeptide derivatives involve the L-form of the various amino acids employed, with the exception of glycine which has, of course, no asymmetric center. Where the compound name or formula has no isomer designation, the name or formula is intended to include the individual isomers, mixtures and racemates thereof.

The symbol $R_1$ can represent hydrogen, in which case the derivative is one of a δ-halo-ε-carboxylysine. Alternatively, it can represent the same amino acids, dipeptide or tripeptide residues indicated for the symbol R at the carboxyl function. It is again intended that a simple amide or peptide bond is created at the δ-amino function of the δ-halo-ε-carboxylysine, utilizing the carboxyl moiety of the particular amino acid(s) employed and the α-amino group of the δ-halo-ε-carboxylysine.

It is to be noted, however, that the symbol R also bears a specific proviso limitation which excludes the possibility of R and $R_1$ simultaneously representing an amino acid, dipeptide or tripeptide. Hence, only one of the terminal carboxyl or amino groups at the 5-position can be substituted at any given time. Thus, when the carboxyl group (R) is substituted by either an amino acid, dipeptide or tripeptide moiety, then $R_1$ must be hydrogen so as to provide a free amino function. Conversely, when the amino group ($R_1$) is similarly substituted, then the symbol R must be hydroxy so as to provide a free carboxyl function.

The symbols X and Y indicated above independently represent hydrogen, fluorine or chlorine with the proviso that both X and Y cannot be hydrogen at the same time. Thus, all of the compounds of this invention are either δ-chloro, δ,δ-dichloro, δ-fluoro, δ,δ-difluoro or δ-chloro-δ-fluoro derivatives of ε-carboxylysine.

The term pharmaceutically acceptable salts includes those non-toxic salts formed with any suitable inorganic or organic acids. In general, the amino acid, dipeptide or tripeptide derivatives are essentially neutral and form acid addition salts only with strong inorganic acids. Illustrative of the inorganic acids that form suitable salts are hydrochloric, hydrobromic, sulfuric and phosphoric acid. On the other hand, the esters of this invention, in addition to forming salts with the inorganic acids above, can form acid metal salts such as sodium monohydrogen orthophosphate and potassium hydrogen sulfate, or salts wih organic acids. Illustrative organic acids include the mono, di- and tricarboxylic acids such as acetic, fumaric, maleic, tartaric, citric, ascorbic, malic, benzoic, hydroxybenzoic, phenylacetic, cinnamic, salicylic and 2-phenoxybenzoic acid.

These salts can be prepared utilizing conventional procedures such as by treating a solution of the δ-halo-ε-carboxylysine derivative in a polar solvent with a stoichiometric quantity of the acid. Inasmuch as both acid and amino functions are present in equal amounts, the compounds of formula (1) may also exist in the form of a neutral zwitterion. In general, the pharmaceutically acceptable salts are crystalline materials which are more soluble in water and hydrophilic solvents in comparison to their corresponding neutral species.

Illustrative compounds which fall within the scope of the invention and which are encompassed by formula (1) above include:
δ-fluoro-ε-carboxylysine
δ-fluoro-ε-carboxylysine methyl ester,
δ-fluoro-ε-carboxylysyl-L-alanine,
δ-fluoro-ε-carboxylysyl-L-alanyl-L-alanine,
δ-fluoro-ε-carboxylysyl-L-alanyl-L-alanyl-glycine,
$N^\alpha$-L-alanyl-δ-fluoro-ε-carboxylysine,
$N^\alpha$-L-alanyl-L-alanyl-δ-fluoro-ε-carboxylysine,
$N^\alpha$-L-alanyl-L-valyl-δ-fluoro-ε-carboxylysine,
δ-chloro-ε-carboxylysine,
δ-chloro-ε-carboxylysine ethyl ester,
δ-chloro-ε-carboxylysyl-L-alanine,
δ-chloro-ε-carboxylysyl-glycyl-glycine,
δ-chloro-ε-carboxylysyl-L-valyl-glycyl-L-valine,
$N^\alpha$-L-alanyl-δ-chloro-ε-carboxylysine,
$N^\alpha$-glycyl-L-alanyl-δ-chloro-ε-carboxylysine,
δ,δ-difluoro-ε-carboxylysine,
δ,δ-difluorolysine-ε-carboxylysine propyl ester,
δ,δ-difluoro-ε-carboxylysyl-L-valyl-L-leucine,
$N^\alpha$-L-valyl-δ,δ-difluoro-ε-carboxylysine,
$N^\alpha$-L-valyl-L-leucyl-δ,δ-difluoro-ε-carboxylysine,
δ,δ-dichloro-ε-carboxylysine,
δ,δ-dichlorolysine-ε-carboxylysine butyl ester,
δ,δ-dichloro-ε-carboxylysyl-L-methionine-glycine,
$N^\alpha$-L-methionyl-δ,δ-difluoro-ε-carboxylysine,
$N^\alpha$-L-methionyl-glycyl-δ,δ-dichloro-ε-carboxylysine,
δ-chloro-δ-fluoro-ε-carboxylysine,
δ-chloro-δ-fluoro-ε-carboxylysine t-butyl ester,
δ-chloro-δ-fluoro-ε-carboxylysyl-L-alanine,
δ-chloro-δ-fluoro-ε-carboxylysyl-L-alanine-L-valine,
$N^\alpha$-L-alanyl-δ-chloro-δ-fluoro-ε-carboxylysine,
$N^\alpha$-L-alanyl-L-valyl-δ-chloro-δ-fluoro-ε-carboxylysine.

The δ-halo-ε-carboxylysines of formula (2) shown below are prepared in a logical sequence utilizing commonly available starting materials.

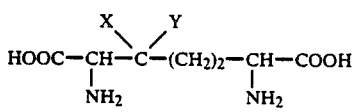

2

The symbols X and Y are as previously indicated. The various alkyl esters, or the amino acid, dipeptide or tripeptide residues can be prepared from the 1,5-diamino-2-halo-1,5-pentanedicarboxylic acids above via standard, art-recognized procedures, or by more specific synthetic approaches described below.

The compound of formula (2), wherein X is hydrogen and Y is chlorine is synthesized in accordance with the synthetic pathway of Scheme I below, wherein Ph represents the phenyl radical.

SCHEME I

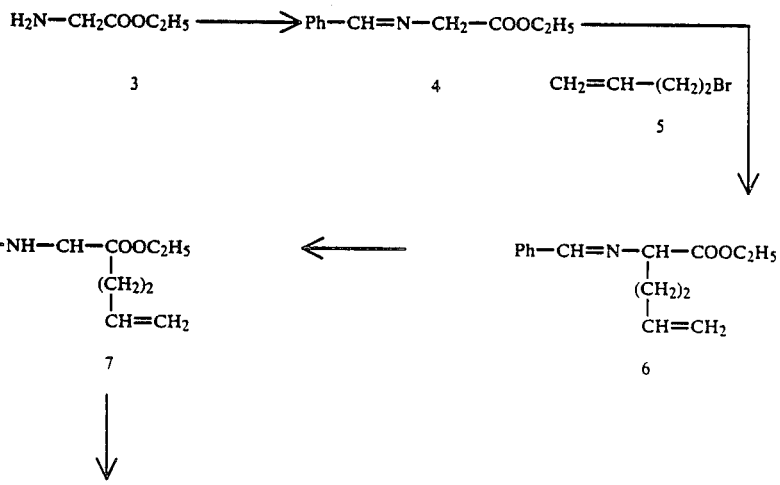

-continued
SCHEME I

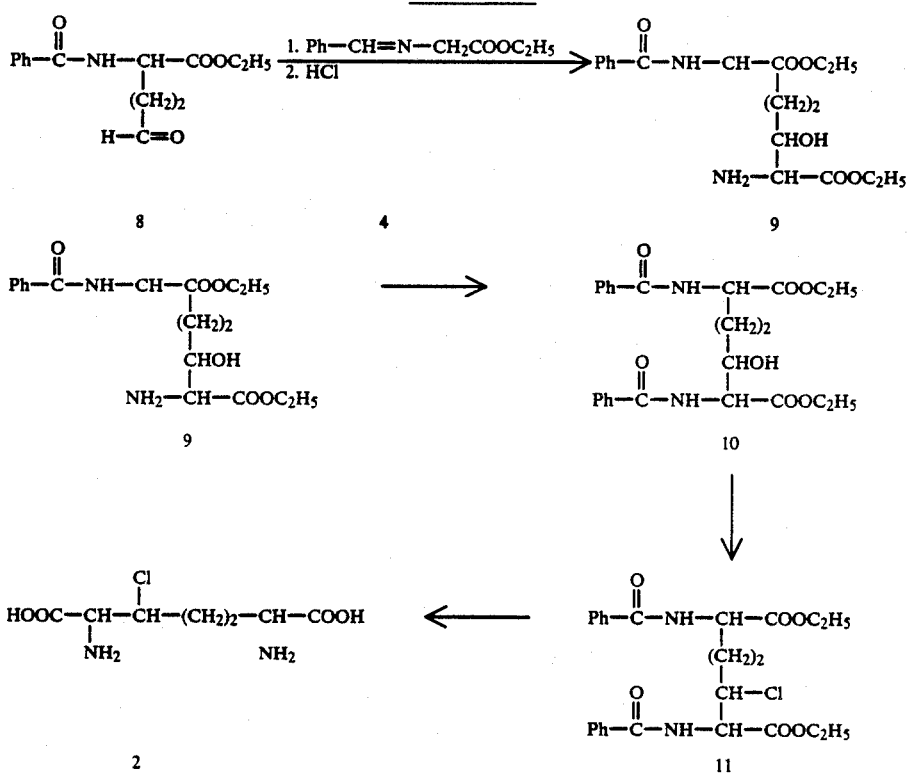

Alkylation of the benzylidene Schiff base 4 of ethyl glycine 3 with 4-bromo-1-butene 5 using lithium diisopropylamide as the base, yields the benzylidene Schiff base of ethyl-2-aminohex-5-ene-oate 6. Acid hydrolysis of 6 and subsequent treatment with benzoyl chloride in the presence of triethylamine results in the formation of ethyl 2-(N-benzoyl)aminohex-5-ene-oate 7. Ozonolysis of 7 proceeds to yield the 4-(N-benzoyl)amino-4-carbethoxy-1-butanal 8. Reaction of 8 with the benzylidene Schiff base of ethyl glycinate 4, using lithium diisopropylamide as base, followed by acid hydrolysis yields $N^\alpha$-benzoyl-$N^\epsilon$-amino-$\delta$-hydroxy-$\epsilon$-carbethoxylysine, diethyl ester 9 which upon subsequent treatment with benzoylchloride in the presence of triethylamine, results in the formation of $N^\alpha,N^\epsilon$-dibenzoyl-$\delta$-hydroxy-$\epsilon$-carbethoxylysine, diethyl ester 10. Chlorination of 10 is achieved by treating 10 with N-chlorosuccinimide and triethylphosphine in tetrahydrofuran to yield the analogous acid 11. Acid hydrolysis of the four protecting groups yields the desired $\delta$-chloro-$\epsilon$-carboxylysine 2 as the dihydrochloride salt.

The compound of formula (2) wherein X is hydrogen and Y is fluorine is synthesized in accordance with the synthetic pathway of Scheme II as shown below, wherein Ph represents the phenyl radical, and various protecting groups are indicated by the following symbols: Pht represents the radical

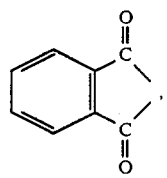

BOC represents the radical

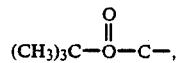

and Mes represents the methanesulfonyloxy radical.

SCHEME II

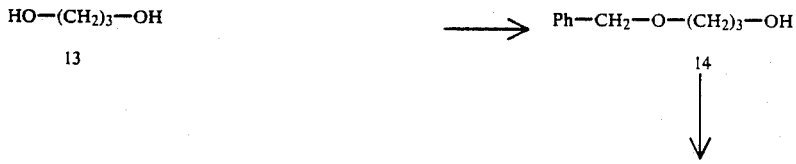

-continued
SCHEME II

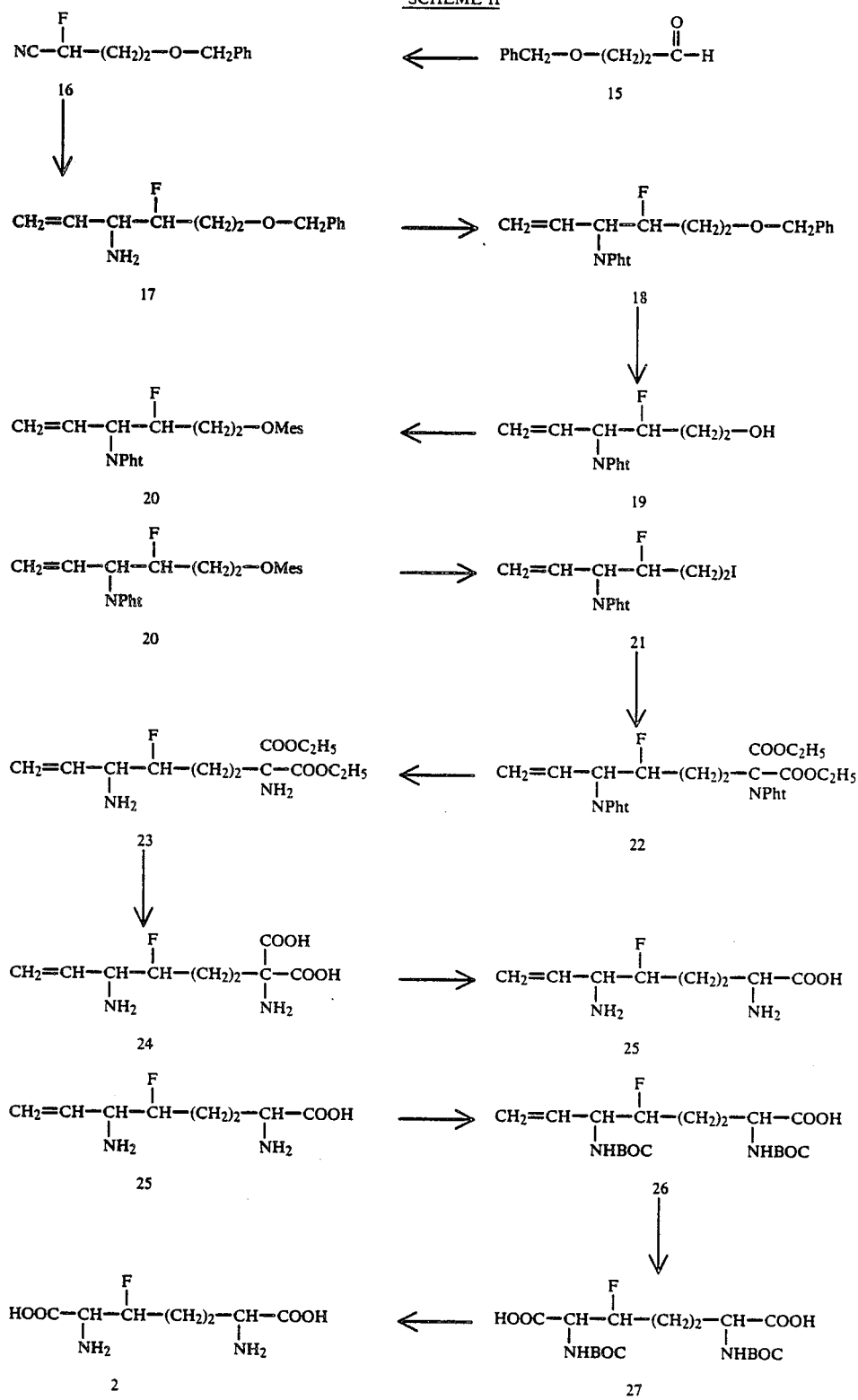

The compound 1,3-propanediol 13 is mono-alkylated to yield the 3-benzyloxy-1-propanol, which is then oxidized by means of oxalyl chloride to the corresponding 3-benzyloxy-1-propanal, 15. Reaction with trimethylsilylcyanide, preferably in the presence of a catalytic amount of zinc iodide, followed by treatment with diethylaminosulfurtrifluoride results in the formation of 4-benzyloxy-2-fluorobutyronitrile, 16.

Reaction of 16 with vinylmagnesium bromide provides an adduct, which is not isolated, but reduced in situ using, for example, sodium borohydride in methanol as a reducing agent, to form 3-amino-4-fluoro-6-benzyloxy-1-hexene, 17. The amino group is protected with N-carbethoxyphthalimide to provide the 3-phthalimido-4-fluoro-6-benzyloxy-1-hexene, 18. Cleavage of the benzyl group using trimethylsilyliodide yields the alcohol 3-phthalimido-4-fluoro-6-hydroxy-1-hexene, 19, and reaction with methanesulfonyl chloride results in the corresponding 3-phthalimido-4-fluoro-6-methanesulfonyloxy-1-hexene, 20. Treatment of 20 with sodium iodide in acetone yields 3-phthalimido-4-fluoro-6-iodo-1-hexene, 21.

Reaction of the iodide 21 with diethylphthalimidomalonate yields ethyl 2,6-diphthalimido-2-ethoxycarbonyl-5-fluoro-7-octenoate, 22. Removal of the amino-protecting groups leads to ethyl 2,6-diamino-2-ethoxycarbonyl-5-fluoro-7-octenoate, 23. Acid hydrolysis of 23 yields 2,6-diamino-2-carboxy-5-fluoro-7-octenoic acid 24, which is decarboxylated by heating with acetic acid in the presence of hydrochloric acid to yield δ-fluoro-ε-vinyllysine, 25. Protection of the amino groups wih di-tert-butyl dicarbonate and triethylamine results in the preparation of Nα,Nε-di-tert-butoxycarbonylamino-δ-fluoro-ε-vinyllysine, 26, which upon oxidation with potassium permanganate yields Nα,Nε-di-tert-butoxycarbonylamino-δ-fluoro-ε-carboxylysine, 27. Removal of the protecting group with HCl results in the desired δ-fluoro-ε-carboxylysine, 2.

The compounds of formula (2), wherein X and Y are chlorine or fluorine are prepared in accordance with the synthetic pathway of Scheme III shown below, wherein the symbols Ph, Pht and BOC have the meanings previously designated.

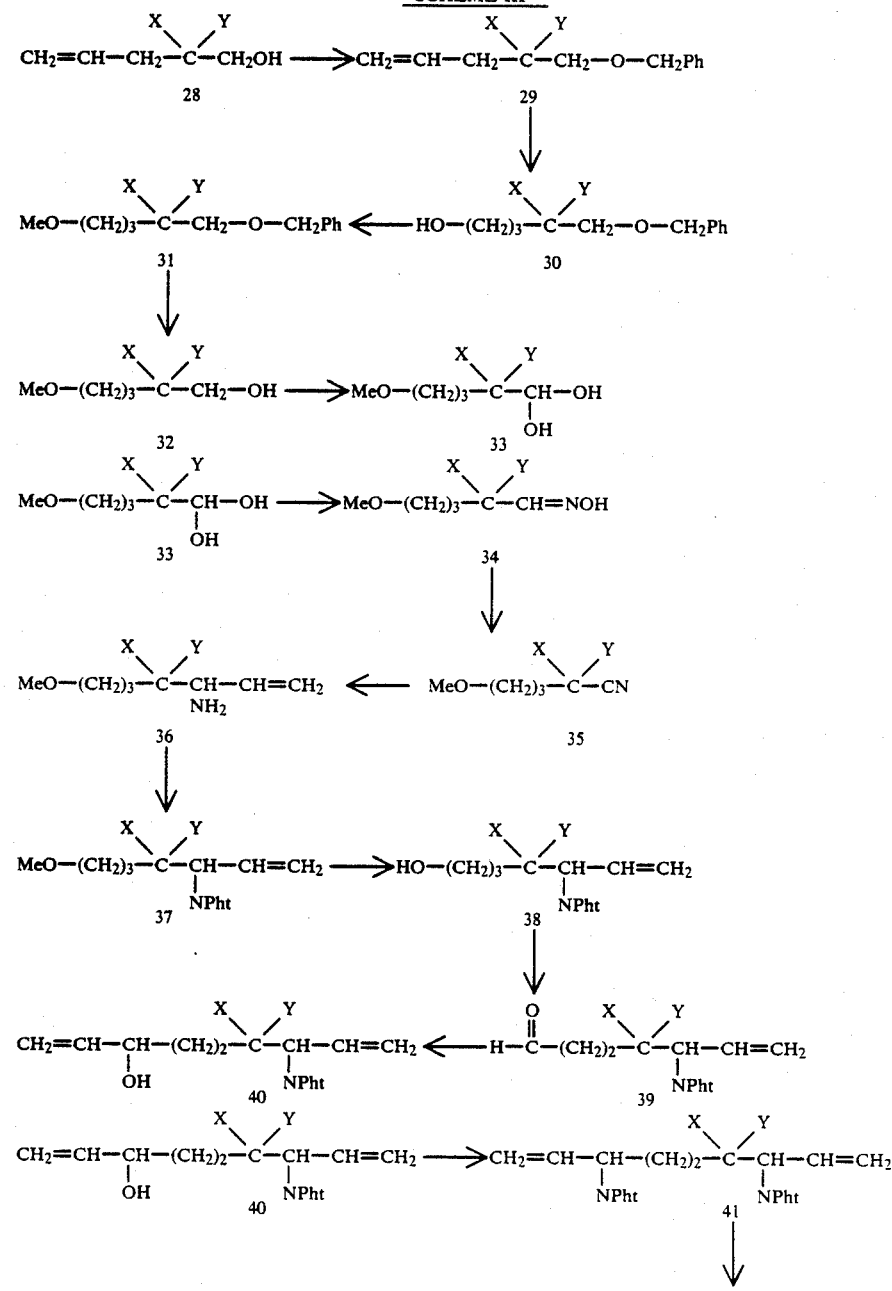

SCHEME III

-continued

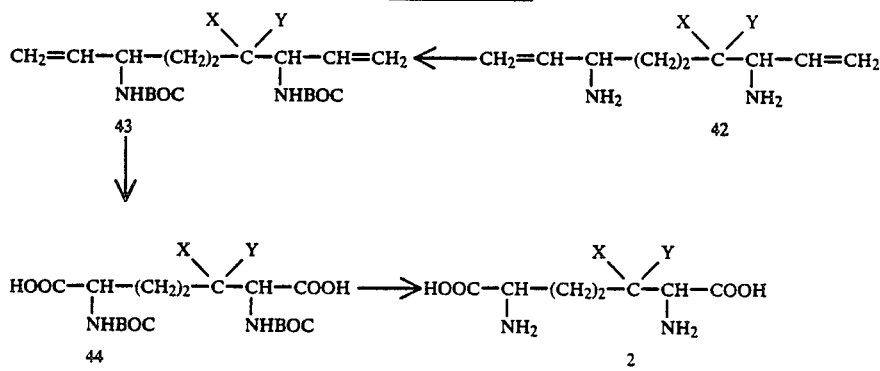

The ethyl esters of 2,2-dihalo-4-pentenoic acid can be reduced with sodium borohydride to provide the 2,2-dihalo-4-pentene-1-ols, 28, which are useful as starting materials for the above reaction scheme. The alcohol functions are first protected using benzyl bromide to form the corresponding 2,2-dihalo-1-benzyloxy-4-pentenes, 29. Hydroboration with sodium borohydride and borontrifluoride/ether complex followed by oxidative work-up of the reaction mixture affords the preparation of the corresponding 2,2-dihalo-1-benzyloxy-5-hydroxypentanes 30. The alcohols 30 are then protected with methyl iodide to yield the corresponding 2,2-dihalo-1-benzyloxy-5-methoxypentanes, 31. Cleavage of the benzyl group using trimethylsilyliodide forms the corresponding 2,2-dihalo-1-hydroxy-5-methoxypentanes, 32.

Oxidation of the alcohols, 32, in the presence of dimethylsulfoxide and oxalyl chloride results in the preparation of the corresponding 2,2-dihalo-5-methoxy-1-pentanal hydrates 33, which are converted to the corresponding 2,2-dihalo-5-methoxy-1-pentanal oximes, 34, by means of an alkaline solution of hydroxylamine hydrochloride. Dehydration of the oximes, 34, by means of thionyl chloride and dimethylaminopyridine in a solvent such as dichloromethane yields the corresponding 2,2-dihalo-5-methoxy-1-valeronitriles, 35.

Reaction of the nitriles, 35, with a vinyl Grignard reagent, such as vinyl magnesium bromide, and the concomitant reduction in situ utilizing sodium borohydride, results in the formation of the corresponding 3-amino-4,4-dihalo-7-methoxy-1-heptenes, 36. Reaction of 36 with N-carbethoxyphthalimide provides the corresponding amino-protected 4,4-dihalo-7-methoxy-3-phthalimido-1-heptenes, 37. Cleavage of the benzyl ether of 37 using trimethylsilyliodide results in the formation of the corresponding 4,4-dihalo-7-hydroxy-3-phthalimido-1-heptenes, 38, which upon oxidation in the presence of dimethylsulfoxide and oxalylchloride yields the aldehydes, 4,4-dihalo-5-phthalimido-6-heptene-1-al, 39.

Reaction of the aldehydes, 39, with vinyl magnesium bromide results in the formation of the corresponding 4,4-dihalo-7-hydroxy-3-phthalimido-1,8-nonadienes, 40. Reaction of 40 with triphenylphosphine, diethyl azodicarboxylate and phthalimide gives the corresponding 4,4-dihalo-3,7-diphthalmido-1,8-nonadienes, 41. Treatment of 41 with hydrazine deprotects these amines to yield the corresponding 3,7-diamino-4,4-dihalo-1,8-nonadienes, 42, which are then reacted with di-tert-butyl dicarbonate to form the corresponding 3,7-di-t-butoxycarbonylamino-4,4-dihalo-1,8-nonadienes, 43. Oxidation of 43 utilizing potassium permanganate affords the 1,5-di-t-butoxycarbonylamino-2,2-dihalo-1,5-pentanedicarboxylic acids, 44. Removal of the amine protecting groups of 44 using dry HCl results in the desired δ,δ-dihalo-ε-carboxylysines, 2.

Compounds of formula 1 wherein X and Y independently are hydrogen, fluorine or chlorine and R is a carboxy-terminal amino acid, dipeptide or tripeptide residue, are prepared in accordance with the synthetic pathway of Scheme IV shown below. In this reaction sequence the symbols X, Y, Ph, Pht and BOC have the meanings previously designated, the symbol t-Bu represents the tert-butyl group, and the symbol -[AA$_n$]-, wherein n is an integer of 1, 2 or 3, represents a radical of an amino acid, dipeptide or tripeptide residue, taken in any sequence, for those amino acids previously described. The term "halo" is taken to include either the monohalo or the dihalo derivatives.

SCHEME IV

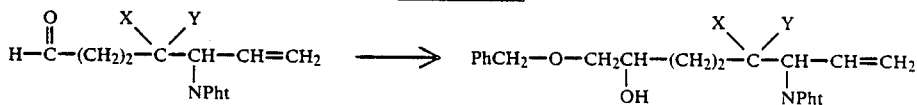

-continued
SCHEME IV

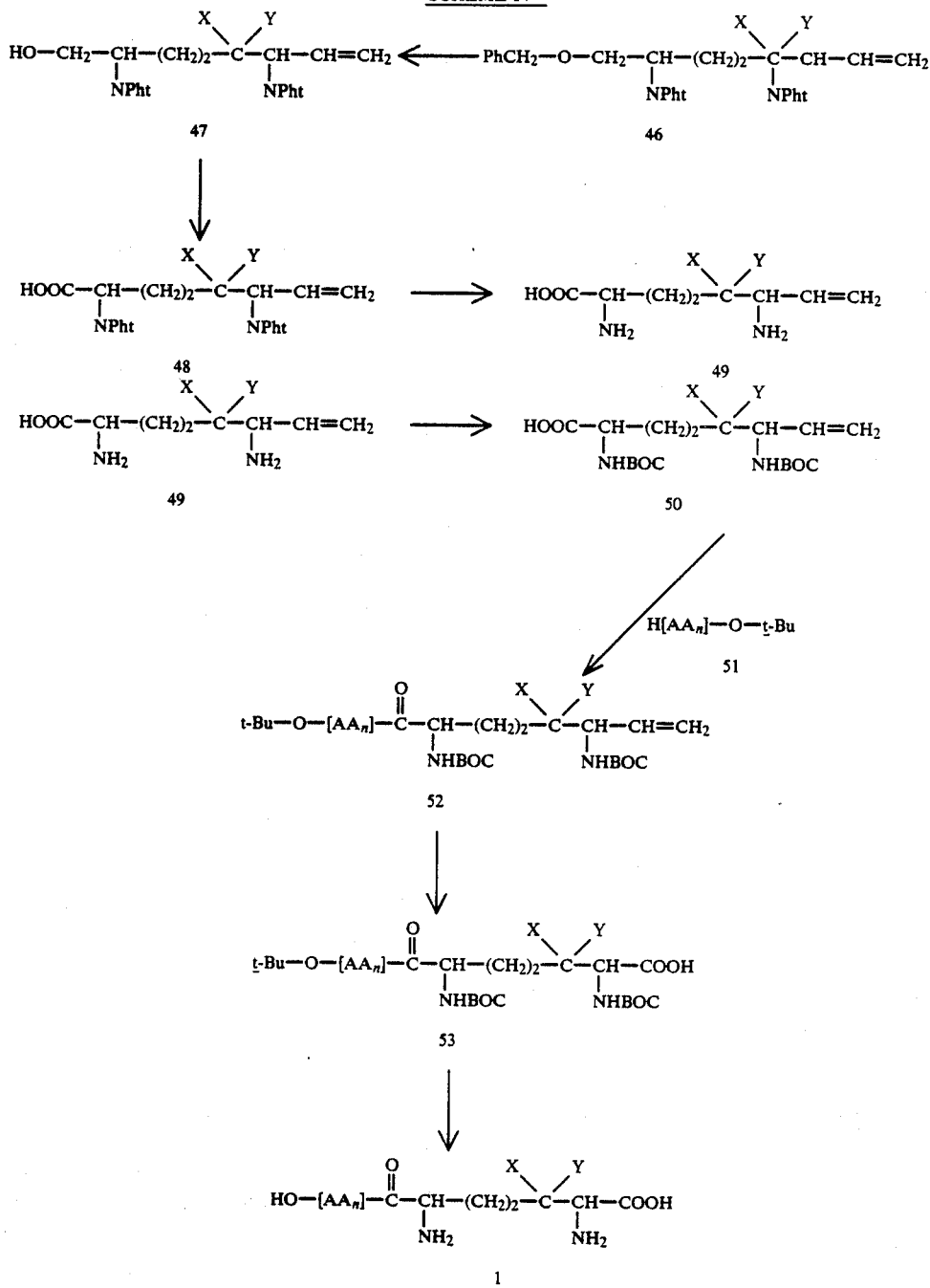

The 4-halo-5-phthalimido-6-heptene-1-al compounds 39, prepared as previously described, are reacted with benzyloxymethyl magnesium chloride to yield the corresponding 1-benzyloxy-2-hydroxy-5-halo-6-phthalimido-7-octenes, 45. The free hydroxyl group is converted to an amino protected group utilizing triphenylphosphine, diethyl azodicarboxylate and phthalimide as reagents to form the corresponding 1-benzyloxy-2,6-diphthalimido-5-halo-7-octenes, 46. Cleavage of the benzyl group with trimethylsilyliodide forms the corresponding 1-hydroxy-2,6-diphthalimido-5-halo-octenes, 47.

Jones' oxidation of 47 utilizing a chromium trioxide/sulfuric acid reagent, results in the formation of the corresponding α,ε-diphthaloyl-δ-halo-ε-vinyllysines, 48. Removal of the amino protecting groups with hydrazine forms the corresponding δ-halo-ε-vinyllysines, 49, which can then be re-protected utilizing di-tert-butyldicarbonate to form the corresponding α,ε-di-t-butoxycarbonyl-δ-halo-ε-vinyllysines, 50.

Protected carboxy-terminal peptides are formed by the reaction of 50 with carboxyl-protected amino acids, dipeptide or tripeptide residues. Preferably the t-butyl esters 51 are employed. Coupling occurs via well-known peptide chemistry, whereby there is obtained the peptides of the corresponding α,ε-di-t-butoxycarbonyl-δ-halo-ε-vinyllysines as the t-butyl esters, 52.

Oxidation of 52 with potassium permanganate results in the formation of the corresponding peptides of α,ε-di-t-butoxycarbonyl-δ-halo-ε-carboxylysines as the t-butyl esters 53, which upon treatment with anhydrous HCl results in the formation of the corresponding desired peptides of the δ-halo-ε-carboxylysines, 1.

Compounds of formula 1 wherein X and Y independently are hydrogen, fluorine or chlorine and $R_1$ is an amino-terminal amino acid, dipeptide or tripeptide residue, are prepared in accordance with the synthetic pathway of Scheme V shown below. In this reaction sequence the symbols X, Y, Ph, Pht, BOC, t-Bu and -[AA$_n$]- have the meanings previously designated. The term "halo" is again taken to include either the monohalo or the dihalo derivatives.

ing triphenylphosphine, diethyl azodicarboxylate and phthalimide as reagents to yield the corresponding 3-phthalimido-6-halo-7-t-butoxycarbonylamino-1,8-nonadienes, 56. Deprotection of the amino group of 56 using methyl hydrazine results in the formation of the corresponding 3-amino-6-halo-7-t-butoxycarbonylamino-1,8-nonadienes, 57.

The protected amino-terminal peptides are formed by the reaction of 57 with amino-protected amino acids, dipeptide or tripeptide residues. Preferably, a butoxycarbonyl amino-protecting group is employed, 58. Coupling occurs via well-known peptide chemistry, whereby there is obtained the corresponding 3(t-butoxycarbonylaminopeptidyl)-6-halo-7-t-butoxycarbonylamino-1,8-nonadienes, 59.

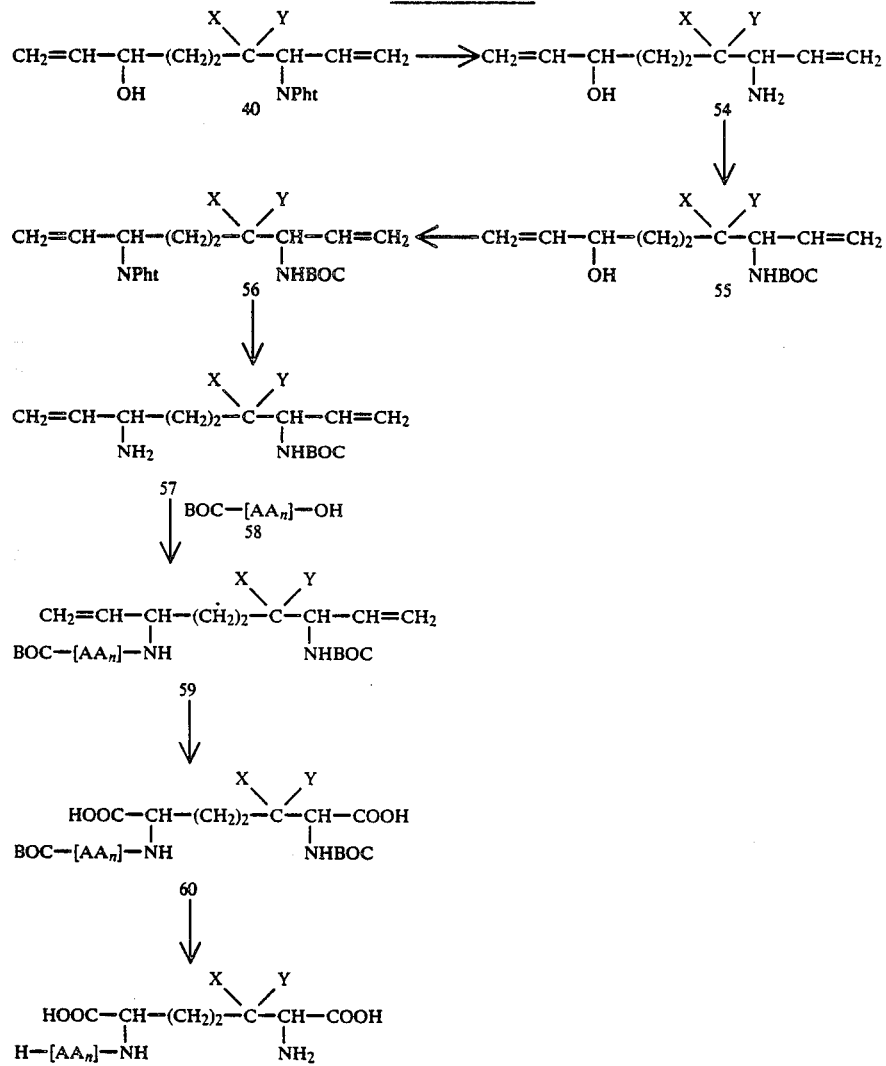

SCHEME V

The 3-hydroxy-6-halo-7-phthalimido-1,8-nonadiene compounds, 40, prepared as previously described, are treated with hydrazine to yield the corresponding 3-hydroxy-6-halo-7-amino-1,8-nonadienes, 54. The amino nitrogen is re-protected using di-tert-butylcarbonate to form the corresponding 3-hydroxy-6-halo-7-t-butoxycarbonylamino-1,8-nonadienes, 55. The free hydroxyl group is converted to an amino-protected group utiliz- Oxidation of 59 with potassium permanganate results in the formation of the corresponding α-(t-butoxycarbonylaminopeptidyl)-ε-t-butoxycarbonylamino-δ-halo-ε-carboxylysines, 60, which on treatment with HCl ether give the desired α-peptidyl-δ-halo-ε-carboxylysines, 1.

Compounds of formula 1 wherein R is $C_1$–$C_4$ alkoxy can be prepared in accordance with the synthetic pathway of Scheme VI below. In this reaction sequence the symbols X, Y, BOC have the same meanings previously designated, the symbol $R_2$ refers to an alkyl group having from 1 to 4 carbon atoms and Z is an appropriate leaving group, preferably iodine. The term "halo" is taken to include both the monohalo and dihalo derivatives.

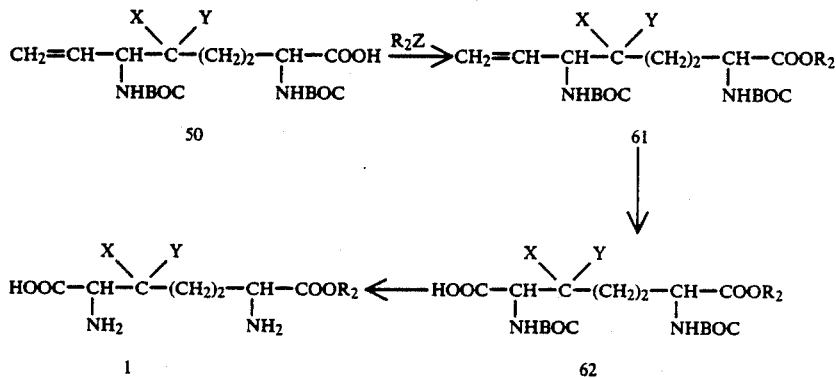

SCHEME VI

Thus, the α,ε-di-t-butoxycarbonyl-δ-halo-ε-vinyllysines, 50, previously described, are treated with dicyclohexylamine and an excess of an alkyl halide $R_2Z$.

Preferably, the appropriate alkyl iodide is employed to yield the corresponding alkyl ester of α,ε-di-t-butoxycarbonyl-δ-halo-ε-vinyllysine, 61. Oxidation of 61 using potassium permanganate results in the formation of the corresponding alkyl ester of α,ε-di-t-butoxycarbonyl-δ-halo-ε-carboxylysine, 62. Treatment of 62 with anhydrous HCl results in the formation of the corresponding alkyl esters of δ-halo-ε-carboxylysine 1.

The compounds of this invention possess anti-bacterial properties in and of themselves, and are effective against certain gram-negative microorganisms as more fully illustrated in Examples VIII and IX. Thus, the compounds of this invention exhibit useful in vitro activity against a broad spectrum of standard laboratory microorganisms, useful in the determination of antibacterial activity against certain infectious bacteria that are pathogenic in nature.

The antibacterial spectrum and minimal inhibitory concentration (MIC) of typical compounds of the present invention are determined by one or more standard techniques. Thus, for example, serial dilutions of the compound being tested are made in tubes of rich medium containing no peptide agonists (Atherton et al., 1979) or in plates containing the same medium plus agar. Series of tubes or plates of agar containing different concentrations of the test compound are inoculated with the cultures utilized to determine activity. After incubation for 24 hours at 37° C., the inoculated tubes or agar plates are examined for the inhibition of bacterial growth and an MIC is determined therefrom.

The compounds of this invention can be utilized both prophylactically and therapeutically. Thus, they may be utilized in cleaning or disinfecting compositions or in standard compositions described below which are useful in combating infections in animals including humans. Concentrations comprising from 0.01 to 1% by weight of such compounds are useful in cleaning or sanitizing compositions for barns or dairy equipment.

The amount of active ingredient for therapeutic administration can vary over a wide range and is dependent upon such factors as the species of animal to be treated, its age, health, sex, weight, nature and severity of the infections to be treated. Generally, the amount of active ingredient to be administered will range from about 0.05 to 3.0 grams and preferably from 0.5 to 2.0 grams per day.

The preferred route of administration is via oral administration. Illustrative dosage levels for oral administration range from 1 to 100 mg per kg of body weight. Preferably, from 10 to 25 mg per kg of the active ingredient are orally administered per day in divided doses. In those instances where the drug is administered via the parenteral route, correspondingly lower doses are employed.

The compounds can be administered in standard dosage unit forms, such as tablets, capsules, dragees, lozenges, elixirs, emulsions, suspensions and various intravenous, intramuscular or intradermal suspensions. The preferred dosage form is that of a tablet or capsule. The amount of active ingredient contained in each dosage unit will, of course, vary depending upon the particular amino acid or peptide derivative of 1,5-diamino-1,5-pentanedicarboxylic acid employed, and the particular dosage form utilized. Generally, a given dosage unit will contain from 10 to 500 mg of the active ingredient in addition to the various pharmaceutical excipients contained therein. Tablets containing from 200 to 400 mg of the active ingredient, are the preferred dosage unit and can be administered b.i.d., or t.i.d. or q.i.d.

In preparing solid dose forms such as tablets, the active ingredient is generally blended with conventional pharmaceutical carriers or excipients such as gelatin, various starches, lactose, calcium phosphate or powdered sugar. The term pharmaceutical carrier as used herein also includes lubricants employed to improve the flow of tablet granulations and to prevent adhesion of tablet material, to the surfaces of tablet dies and punches. Suitable lubricants include, for example, talc, stearic acid, calcium stearate, magnesium stearate and zinc stearate. Also included within the definition of a pharmaceutical carrier as used herein are disintegrating agents added to assist the breakup and dissolution of tablets following administration, and coloring and/or flavoring agents to enhance the aesthetic qualities of the tablets and make them more acceptable to the patient.

Suitable liquid excipients for the preparation of liquid dosage unit forms include water and alcohols such as ethanol, benzyl alcohol and the polyethylene alcohols, either with or without the addition of a surfactant. In general, the preferred liquid excipients particularly for injectable preparations, include water, saline solution, dextrose and glycol solutions such as an aqueous propylene glycol or an aqueous solution of polyethylene glycol. Liquid preparations to be used as sterile injectable solutions will ordinarily contain from about 0.5 to about 25% by weight, and preferably from about 1 to about 10% by weight, of the active ingredient in solution. In certain topical and parenteral preparations, various oils are utilized as carriers or excipients. Illustrative of such oils are mineral oils, glyceride oils such as lard oil, cod liver oil, peanut oil, sesame oil, corn oil and soybean oil. For insoluble compounds suspending agents may be added as well as agents to control the viscosity, as for example, magnesium aluminum silicate or carboxymethyl-cellulose. In addition to these excipients, buffers, preservatives and emulsifying agents may also be added.

The proportion of the active ingredient employed in parenteral dosage unit forms ranges from 0.05 to about 20% by weight of the total liquid composition, the remaining component or components comprising any of the various pharmaceutical excipients previously mentioned. In order to minimize or eliminate irritation at the site of injection, such compositions may contain a non-ionic surfactant having a hydrophile-lipophile balance (HLB) of from about 12 to about 17. The quantity of surfactant in such formulations ranges from about 5 to about 15% by weight. The surfactant can be a single component having the above-identified HLB, or a mixture of two or more components having the desired HLB. Illustrative of surfactants useful in parenteral formulations are the class of polyoxyethylene sorbitan fatty acid esters as, for example, sorbitan monooleate and the high molecular weight adducts of ethylene oxide with a hydrophobic base, formed by the condensation of propylene oxide with propylene glycol.

The invention described herein is more particularly illustrated in conjunction with the following specific preparations, but is not necessarily limited thereto.

EXAMPLE I

PREPARATION OF 1,5-DIAMINO-2-CHLORO-1,5-PENTANEDICARBOXYLIC ACID (δ-CHLORO-ε-CARBOXYLYSINE)

Benzyidine Schiff Base of Ethyl Glycinate (4)

Ethyl glycinate hydrochloride (60.2 g, 0.43M), freshly distilled benzaldehyde (48 ml, 0.43M), and anhydrous MgSO$_4$ (30 g) are suspended in dry CH$_2$Cl$_2$ (600 ml). To this suspension is added Et$_3$N (120 ml, 0.86M) in dry CH$_2$Cl$_2$ (100 ml) over about 2 hours. After addition the mixture is stirred at room temperature overnight. The mixture is filtered and evaporated to dryness in vacuo. The formed mushy solid is resuspended in Et$_2$O and removed by filtration. The Et$_2$O layer is washed with H$_2$O (3×200 ml), saturated aqueous NaCl (1×200 ml), dried over anhydrous MgSO$_4$, filtered and evaporated to dryness in vacuo to leave 81.2 g (99% yield) of a yellow oil. $^1$H-N.M.R. (CDCl$_3$/TMS): δ=1.30 (t, 3H, —CH$_2$CH$_3$); 4.23 (q, 2H, —CH$_2$CH$_3$); 4.40 (s, 2H, —CH$_2$—); 7.20–7.80 (m, 5H, Ph); 8.25 ppm (s, 1H, —CH=N—).

Ethyl 2-(N-benzylidene)aminohex-2-ene-oate (6)

Diisopropylamine (80.2 ml, 0.57M) is added to anhydrous THF (500 ml) and cooled to −10° C. Then 2.4M n-BuLi (237.5 ml) is added slowly, keeping the temperature at −10° C. After complete addition the orange reaction mixture is cooled at −10° C. and stirred for another 15 minutes before reducing the temperature to −78° C. Hexamethyl phosphoramide (HMPA) (100 ml, 0.57M) is then added, followed by the addition of ethyl N-benzylidene glycinate (100 g, 0.52M) dissolved in anhydrous THF (200 ml). After the addition is complete, the reaction mixture is stirred at −78° C. for an additional 15 minutes before adding 4-bromo-1-butene (5) (70.7 g, 0.52M). The reaction mixture is allowed to warm to room temperature and stirring is continued for another 4 hours. It is then poured into ice cold 5% NH$_4$Cl solution (1 l) and extracted with CHCl$_3$ (3×600 ml). The combined extracts are backwashed with H$_2$O (3×200 ml), saturated NaCl solution (3×200 ml), dried over anhydrous MgSO$_4$, filtered and evaporated to yield an orange oil. This oil was kugelrohred and the desired product collected to give 97.1 g (76% yield) of (6). $^1$H-N.M.R. (CDCl$_3$/TMS): δ=1.28 (t, 3H, —CH$_2$CH$_3$); 1.97–2.20 (m, 4H, —CH$_2$—CH$_2$—); 3.82–4.18 (apparent m, 1H, >C$\underline{H}$—CO$_2$Et, overlaps ethyl ester quartet); 4.25 (q, 2H, —CH$_2$CH$_3$); 4.80–5.25 (m, 2H, —CH=C$\underline{H}_2$); 5.33–6.19 (m, 1H, —C$\underline{H}$=CH$_2$); 7.10–7.94 (m, 5H, Ph); 8.28 ppm (s, 1H, —N=CH—).

Ethyl-2-(N-benzoyl)aminohex-2-ene-oate (7)

Schiff base (6) (97.1 g, 0.4M) is dissolved in THF (250 ml) and shaken in a separatory funnel with 10% aqueous HCl (1 l) for 5 minutes. This mixture is washed with Et$_2$O (3×250 ml), the aqueous phase separated, neutralized with solid NaHCO$_3$ and extracted with CHCl$_3$ (3×250 ml). The combined CHCl$_3$ extracts are dried over anhydrous MgSO$_4$, filtered and evaporated to yield a pale yellow liquid, 57.9 g (93% yield). $^1$H-N.M.R. (CDCl$_3$/TMS): δ=1.30 (t, 3H, —CH$_2$CH$_3$); 1.50 (s, 2H, —NH$_2$); 1.47–2.38 (m, 4H, —CH$_2$CH$_2$—); 3.43 (dd, 1H, >C$\underline{H}$—CH$_2$—, J=6 and 8 Hz); 4.20 (q, 2H, —CH$_2$CH$_3$); 4.80–5.20 (m, 2H, —CH=C$\underline{H}_2$); 5.45–6.20 ppm (m, 1H, —C$\underline{H}$=CH$_2$). The latter is stirred in CH$_2$Cl$_2$ (600 ml) containing Et$_3$N (51 ml, 0.37M) and cooled in an ice bath before benzoyl chloride (43 ml, 0.37M) in CH$_2$Cl$_2$ (100 ml) is added dropwise over a period of ½ hour. The reaction mixture is allowed to warm to room temperature and stirred overnight. The formed Et$_3$N HCl is removed by filtration and the filtrate is evaporated to dryness. The residue is taken up in Et$_2$O, filtered, washed with 5% aqueous HCl (3×100 ml), saturated aqueous NaHCO$_3$ (3×100 ml), saturated aqueous NaCl (3×100 ml), dried over anhydrous MgSO$_4$ and evaporated to dryness. The white solid thus obtained is recrystallized twice from Et$_2$O/hexane to yield 64.3 g of the desired product (7) (67% yield) m.p. 68°–70° C. The two recrystallizations are required in order to remove an impurity which turned out to be the bis alkylated material (m.p. 46°–49° C.) that is carried along. $^1$H-N.M.R. (CDCl$_3$/TMS): δ=1.3 (t, 3H, —CH$_2$CH$_3$); 1.80–2.34 (m, 4H, —CH$_2$C$\underline{H}_2$—); 4.28 (q, 2H, —CH$_2$CH$_3$); 4.64–5.15 (m, 3H, >CH=CH$_2$ and CHCO$_2$Et); 5.53–6.0 (m, 1H, CHC$\underline{H}_2$); 6.70 (d, 1H, >NH); 7.30–7.85 ppm (m, 5H, Ph).

C$_{15}$H$_{19}$NO$_3$ Calculated: C 68.94, H 7.33, N 5.39; (261.32) Found: C 68.94, H 7.29, N 5.14

I.R. (KBr): 3330, 1750, 1650, 1550, 1208, 1160, 715 cm$^{-1}$.

4-(N-benzoyl)amino-4-carbethoxy-1-butanal (8)

Alkene (7) (5.0 g, 19.1 mM) is dissolved in 25% MeOH/CH$_2$Cl$_2$ solution (500 ml) and after cooling to −78° C., ozone is bubbled through the reaction mixture until a light blue color persists. Nitrogen is then passed through the solution to remove excess ozone. Me$_2$S (3.75 ml) and pyridine (several drops) are added and the solution is allowed to warm to room temperature. Stirring under nitrogen at room temperature is continued overnight. The reaction mixture is evaporated and the oily residue is purified by flash chromatography on silica gel (3% acetone/CH$_2$Cl$_2$) to yield an oil which crystallizes on standing, 2.9 g (58% yield). An analytical sample is obtained by recrystallization from Et$_2$O (m.p. 74°–78° C.). 'H-N.M.R. (CDCl$_3$/TMS): δ=1.28 (t, 3H, —CH$_2$CH$_3$); 1.70–2.80 (m, 4H, —CH$_2$CH$_2$—); 4.20 (q,2H, —CH$_2$CH$_3$); 4.45–5.00 (m, 1H, >CHCO$_2$Et); 6.95–7.90 (m, 5H, Ph); 9.80 ppm (s, 1H, —CHO).

C$_{14}$H$_{17}$NO$_4$ Calculated: C 63.87, H 6.51, N 5.32; (263.29) Found: C 63.67, H 6.49, N 4.97

I.R. (KBr): 3390, 1735, 1725, 1640, 1520, 1020, 720 cm$^{-1}$.

2-amino-3-hydroxy-6-(N-benzoyl)aminoheptanedioic acid, diethyl ester (9)

Diisopropylamine (2.34 ml, 16.7 mmoles) is added to anhydrous THF (75 ml) and cooled to −10° C. At this point 2.24M n-BuLi (6.8 ml, 15.2 mmoles) is added slowly. After complete addition the reaction mixture is stirred for 10 minutes before being cooled to −78° C. At that temperature ethyl N-benzylideneglycinate (4) (2.9 g, 15.2 mmoles) is added and stirring is allowed to proceed for 15 minutes before aldehyde (8) (4.0 g, 15.2 mmoles), dissolved in anhydrous THF (25 ml), is added dropwise to the yellow anion. After complete addition the reaction is stirred another 1½ hours before being poured into cold 5% aqueous NH$_4$Cl. This mixture is extracted with CHCl$_3$ (3×100 ml). The combined extracts are washed with saturated aqueous NaCl, dried over MgSO$_4$, filtered and evaporated to dryness. The oily residue is taken up in THF (300 ml) and shaken with 5% aqueous HCl (200 ml) in a separatory funnel. This mixture is washed with Et$_2$O (3×100 ml), basified with solid NaHCO$_3$ and extracted with CHCl$_3$ (3×150 ml). The combined extracts are washed with saturated aqueous NaCl (1×150 ml), dried over MgSO$_4$, filtered and evaporated to dryness in vacuo to yield 4.0 g (72% yield) of the desired compound as a yellow glass. 'H-N.M.R. (CHCl$_3$/TMS): δ=1.20 (t, 3H, —CH$_2$CH$_3$); 1.28 (t, 3H, —CH$_2$CH$_3$); 1.45–2.20 (m, 4H, —CH$_2$CH$_2$—); 2.46 (broad s, 2H, —NH$_2$); 3.18–4.00 (m, 2H, >CH—NH$_2$, CHOH); 4.19 (q, 2H, —CH$_2$CH$_3$); 4.25 (q, 2H, —CH$_2$CH$_3$); 4.53–5.08 (m, 1H, >CH—NH—); 7.05–7.97 ppm (m, 5H, Ph).

2,6-di-(N-benzoyl)amino-3-hydroxyheptanedioic acid, diethyl ester (10)

Amine (9) (4.0 g, 10.9 mM) is taken up in CH$_2$Cl$_2$ (150 ml), cooled in an ice bath, and treated with Et$_3$N (1.67 ml, 12 mM). Benzoyl chloride (1.27 ml, 10.9 mM) is added slowly over a period of 5 minutes and stirring continued at 4° C. for 1 hour. The reaction is warmed to room temperature and stirred overnight. This mixture is washed with 5% aqueous HCl (3×100 ml), saturated aqueous NaCl (3×100 ml), dried over anhydrous MgSO$_4$ and evaporated to dryness in vacuo to yield a white foam. The latter is purified by flash chromatography on silica gel eluting with 12% acetone/CH$_2$Cl$_2$ to yield 3.0 g (59% yield) of the desired product as a white foam. 'H-N.M.R. (CDCl$_3$/TMS): δ=1.19 (t, 3H, —CH$_2$CH$_3$); 1.22 (t, 3H, —CH$_2$CH$_3$); 1.40–2.27 (m, 4H, —CH$_2$CH$_2$—); 4.19 (2q, 4H, —CH$_2$CH$_3$); 4.00–5.00 (4H, 10H, 2>CHCO$_2$Et, CHOH); 6.90–7.86 ppm (m, 12H, 2NH and 2Ph).

2,6-di-(N-benzoyl)amino-3-chloroheptanedioic acid, diethyl ester (11)

To a stirred solution of N-chlorosuccinimide (0.17 g, 1.28 mM) in anhydrous THF (20 ml) is added a solution of Ph$_3$P (0.33 g, 1.28 mM) in anhydrous THF (10 ml) dropwise. An exothermic reaction occurs with concomitant separation of a pink, milky solid. To this suspension is added alcohol (10) (0.6 g, 1.28 mM) in anhydrous THF (5 ml). After 1 hour the reaction solution is a clear pink. After one further hour the mixture is poured into Et$_2$O/CH$_2$Cl$_2$ (1—1, 50 ml), dried over anhydrous MgSO$_4$, filtered and evaporated to dryness in vacuo to give a pink foam. This foam is purified by flash chromatography on silica gel eluted with 5% acetone/CH$_2$Cl$_2$ to yield 170 mg of the desired product as a white foam (28% yield). 'H-N.M.R. (CDCl$_3$/TMS): δ=1.28 (t, 3H, —CH$_2$CH$_3$); 1.30 (t, 3H, —CH$_2$CH$_3$); 1.70–2.50 (m, 4H, —CH$_2$CH$_2$—); 4.28 (2q, 4H, —CH$_2$CH$_3$); 4.00–5.33 (m, 3H, CHCl, 2CHCO$_2$Et); 6.80–8.00 mmp (m, 12H, 2NH and 2Ph).

C$_{25}$H$_{29}$ClN$_2$O$_6$ Calculated: C 61.41, H 5.98, N 5.73, Cl 7.25; (488.97) Found: C 61.22, H 6.17, N 5.54, Cl 7.11

M.S.: m/e=489 (M+), 379, 294, 246, 105, 36.

1,5-diamino-2-chloro-1,5-pentanedicarboxylic acid, dihydrochloride (2)

(δ-chloro-ε-carboxylysine, dihydrochloride)

Tetraprotected amino acid (11) (118 mg, 0.24 mM) is refluxed in 6N HCl (20 ml) for 8 hours. After cooling the aqueous solution was washed with Et$_2$O (3×25 ml) and evaporated to dryness in vacuo to yield the desired compound as a very hygroscopic white foam, 64 mg (89% yield).

EXAMPLE II

PREPARATION OF 1,5-DIAMINO-2-FLUORO-1,5-PENTANEDICARBOXYLIC ACID (δ-FLUORO-ε-CARBOXYLYSINE)

3-Benzyloxy-1-propanol (14)

In a 2 L flask, a solution of 1,3-propane-diol (3) (38 g, 0.5 moles) and benzyl bromide (85.5 g, 0.5 moles) in dry tetrahydrofuran (500 mL) is cooled to 0° C. (internal temperature) using ice/salt mixture. Potassium-t-butoxide (56 g, 0.5 moles) is added in portions, maintaining the temperature below +20° C. The mixture is stirred at room temperature overnight, then poured into 2N HCl (1 L) and water (1 L). After saturating with NaCl, the mixture is extracted with ether (1.5 L). The organic phase is washed with water (3×), dried (Na$_2$SO$_4$) and evaporated to give an oil (81 g). This is distilled (oil pump) to give pure 14 as a colourless liquid: 58.5 g (70%), bp about 0.05 95°–105° C.

3-Benzyloxy-1-propanal (15)

Under nitrogen, a solution of DMSO (8.4 mL, 118 mmoles) in dry dichloromethane (125 mL) is cooled to −60° C., and oxalyl chloride (5 mL, 59 mmoles) in $CH_2Cl_2$ (40 mL) is added slowly. After stirring for 5 min at $-50°$ C., 3-benzyloxy-1-propanol (14), 8.9 g, 53.7 mmoles) in $CH_2Cl_2$ (27 mL) is added at $-60°$ C. Stirring is continued for 15 min, then triethylamine (47 mL) is added slowly at $-60°$ C. After 5 min at this temperature, the mixture is allowed to warm up to room temperature. After addition of 0.5N HCl and phase separation, the organic phase is washed with water until neutral. Drying ($Na_2SO_4$) and evaporation gives the crude aldehyde as an oil: 10.6 g. Distillation under vacuum gives pure 15: 6.54 g (74%), bp 170° C. (15 mm Hg).

4-Benzyloxy-2-fluoro-butyronitrile (16)

Under nitrogen, a mixture of trimethylsilyl cyanide (1.335 mL, 10 mmoles) and 15 (1.64 g, 10 mmoles) is heated at 100° C. for 6 hours. The reaction is monitored by NMR (88% conversion after 6 hours). The mixture is cooled to 5° C. (ice bath), and $CH_2Cl_2$ (12 mL) is added, followed by diethylaminosulfurtrifluoride, (0.46 g, 9.1 mmoles), dissolved in $CH_2Cl_2$ (8 mL) at about 5° C.

The mixture is stirred at room temperature for 1½ hour, then poured on ice/water, washed with 0.5N HCl, water saturated $NaHCO_3$, twice with 2N HCl, and finally with water. Drying and evaporation yields a brown oil (1.7 g). This is purified by filtration over $SiO_2$ Merck 9385 (1.7 g, height of silica: 15 cm) using pet. ether/AcOEt 9:1 until about 4 mL are eluted, then 10 mL of pet. ether. Evaporation gives 1.25 g (65%) of still brown coloured oil which according to NMR is pure enough.

3-amino-4-fluoro-6-benzyloxy-1-hexene (17)

Under nitrogen, vinyl magnesium bromide is prepared from vinyl bromide (16 g, 150 mmoles) and magnesium turnings (3.64 g, 150 mmoles) in tetrahydrofuran (about 300 mL). According to titration (HCl/NaOH, phenolphthalein), the Grignard is 0.485M. 246 mL (119 mmoles) of this Grignard are stirred and 16 (23.0 g, 119 mmoles) dissolved in some tetrahydrofuran is added, keeping the internal temperature at 0° C. Stirring is continued at this temperature for 45 Min, then a solution of sodium borohydride (4.52 g) in cold ($-40°$ C.) methanol/water (500 mL/10 mL) is prepared and added to the Grignard reaction mixture which is precooled to approximately $-20°$ C. The mixture is allowed to warm up to 0° C. (about 30 min) and hydrolyzed with 6N HCl (about 70 mL, pH about 6-7). The tetrahydrofuran and methanol are evaporated (bath temperature 25°-30° C.), some water is added, and the mixture is extracted with ether. After basifying strongly with NaOH, 17 is extracted with ether, the organic phase is dried ($Na_2SO_4$) and evaporated to yield 17 as an oil: 16.6 g (62%).

3-phthalimido-4-fluoro-6-benzyloxy-1-hexene (18)

Compound 17 prepared above (16.6 g, 74.4 mmoles) and N-carbethoxphthalimide 16.3 g, 74.4 mmoles) are dissolved in benzene (240 mL) and kept at room temperature overnight. The solvent is evaporated, and the residual oil is dissolved in dry dichloromethane (Baker Blue Label) and treated with triethylamine (10.5 mL) for several hours at room temperature. After washing with 1N HCl and evaporation, the product is purified by flash chromatography ($SiO_2$ Merck 9385, 200 g, ethyl acetate/pet. ether 20:80); fractions 5 to 14 are pooled to yield pure 18: 20.0 g (76%) as an oil.

3-phthalimido-4-fluoro-6-hydroxy-1-hexene (19)

Compound 18 prepared above (20.0 g, 56 mmoles) is dissolved in dry dichloromethane (Baker Blue Label) and treated with trimethylsilyliodide (11.2 g, 56 mmoles) overnight under nitrogen. The mixture is washed with $NaHCO_3$, then with water, dried, and evaporated. The oil obtained, 19, is purified by filtration over silica, washing first with pet. ether (3 L), then with ethyl acetate: 15 g (about quantitative).

3-phthalimido-4-fluoro-6-methanesulfonyloxy-1-hexene (20)

The proceeding compound, 19, (15 g) in dry dichloromethane (100 mL) and dry pyridine (33 mL, dist. from KOH) is treated at room temperature with methane-sulfonylchloride (6.4 g, 56 mmoles) overnight. The mixture is washed with 6N HCl, then with water, dried and evaporated to yield 20 as an oil: 19 g.

3-phthalimido-4-fluoro-6-iodo-1-hexene (21)

Crude 20 prepared above (19 g, 56 mmoles), acetone (48 mL) and sodium iodide (16.8 g) are refluxed for three hours, thereby adding about 20 more mL of acetone to the solidifying mixture. Filtration and evaporation gives a residue which is dissolved in ether and washed with $NaHSO_3$, then with water. Drying and evaporation gives 21 as an oil: 18.0 g (overall yield from 19: 85%). This material is used for the next step without further purification.

Ethyl 2,6-diphthalimido-2-ethoxycarbonyl-5-fluoro-7-octenoate (22)

To a solution of diethylphthalimidomalonate (Fluka B 260895, 14.7 g) in dry DMF (dist. from $CaH_2$, 50 mL) is added solid potassium-t-butoxide (5.3 g), and the suspension is stirred until homogeneous (20 min, slightly exothermic). Previously prepared compound 21 (18 g, 48 mmoles), dissolved in some DMF, is added, and the mixture is heated under nitrogen at 55°-60° C. over the weekend.

The DMF is stripped (oil pump), the residue taken up in ether and washed with water, 1N HCl, and water again. Drying and evaporation gives crude 22 as an oil (29 g). Flash chromatography (AcOEt/pet. ether 20:80; $SiO_2$ Merck 9385 300 g, fraction size: 100 mL) gives the pure compound 22 (17.5 g, 66%).

Ethyl 2,6-diamino-2-ethoxycarbonyl-5-fluoro-7-octenoate (23)

The foregoing compound 22 (17.5 g, 31.8 mmoles) and a 1M solution of $N_2H_4.H_2O$ in dioxane/ethanol 4:1 (35 mL, 2 equivalents) are stirred and heated at about 90° C. After 3 hours, a yellow precipitate is formed, and the mixture is allowed to cool to room temperature. The precipitate is filtered and the filtrate is evaporated to yield an oil. The oil and the precipitate are united and heated with ethanol (310 mL) and conc. HCl (18.6 mL) at 90° C. for 3 hours. After cooling, phthalhydrazide is filtered and the solution is evaporated. Dissolving in water, filtration, evaporation, dissolving in ethanol, evaporating again and drying (oil pump) yields a yellow foam: 11.5 g (about 100%). Thin layer chromatography (ethanol/ammonia 80/20) shows a second spot (presumably some ester cleaved). The compound 23 is utilized for the next step without further purification.

2,6-diamino-2-carboxy-5-fluoro-7-octenoic acid (24)

The crude material 23 (11.5 g, about 31 mmoles since some solvent left) is dissolved in ethanol (150 mL) and 2N NaOH (150 mL) and stirred at room temperature for 3 hours. The mixture is neutralized with conc. HCl (about 25 mL) with cooling, then acidified (HCl). After evaporation and drying, the residue is dissolved in ethanol, filtered through millipore, and evaporated again. Dissolving in water, filtration, and evaporation yields a solid (11 g, 2 g more than theory). This is dissolved in isopropanol (130 mL) and treated with propylene oxide (6.5 mL, 3 equivalents). Crude 24 (7.2 g, somewhat more than theory) is collected. Thin layer chromatography (ethanol/NH$_4$OH 80/20 revelation ninhydrin) indicates the presence of some decarboxylated product. The compound 24 is used without further purification. Recrystallization from water/ethanol is possible. Caution: no heating!

2,6-diamino-5-fluoro-7-octenoic acid (25)

The compound 24 (7 g, about 30 mmoles) is heated with acetic acid containing 6% of conc. HCl (330 mL) at 120° C. for 1 hour. Stripping followed by two evaporations with CCl$_4$, two with isopropanol, and drying (oil pump) yields a yellow foam, which is hygroscopic. This is dissolved in isopropanol and converted to the monohydrochloride by treatment with propylene oxide: white solid: 6.0 g (89%).

Thin layer chromatography (ethanol/NH$_4$OH 80/20, indicator: ninhydrin): one major spot plus traces.

2,6-di-tert-butoxycarbonylamino-5-fluoro-7-octenoic acid (26)

To a solution of 25 prepared above (2.0 g, 8.85 mmoles) in water (20 mL) and tetrahydrofuran (32 mL), di-tert-butyl dicarbonate (5.75 g, 26.55 mmoles) and triethylamine (5.30 g, 52.5 mmoles) are added. After stirring at room temperature for 14 hours, the tetrahydrofuran is stripped and the aqueous solution is extracted with ether (2×10 mL).

The aqueous phase is acidified with saturated KHSO$_4$ solution to a pH of 2–3 with vigorous stirring. Extraction with ethyl acetate (4×20 mL), washing with water (2×10 mL), drying (MgSO$_4$) and evaporation (30° C./20 mm Hg, then 30° C./0.05 mm Hg) yields 26 as a colorless oil: 2.7 g (78%). Thin layer chromatography (AcOEt+1 drop of acetic acid): one spot+traces.

3-fluoro-2,6-di-tert.-butoxycarbonylaminopimelic acid (27)

(N$^\alpha$,N$^\epsilon$-di-tert-butoxycarbonyl-δ-fluoro-ε-carboxylysine)

A solution of 5-fluoro-2,6-di-tert.-butoxycarbonylamino-7-octenoic acid (220 mg, 0.56 mmoles), in acetone (2 mL) is added to a solution of potassium permanganate (267 mg) in water (9 mL) and acetic acid (2 mL). After stirring at room temperature overnight, sodium bisulfite is added, and the solution is saturated with sodium chloride and extracted with ether. After washing with a sodium bisulfite solution, drying and evaporation gives the title compound as a white foam: 230 mg.

3-fluoro-2,6-diaminopimelic acid (28)

(δ-fluoro-ε-carboxlysine)

3-fluoro-2,6-di-tert.-butoxycarbonylaminopimelic acid (940 mg, 2.3 mmoles) is dissolved in ether saturated with HCl gas, and the mixture is stirred overnight. The white crystals are filtered off and dissolved in isopropanol/ethanol. After filtration through a membrane filter (Millipore), propylene oxide (0.6 mL) is added. The precipitate is stirred with isopropanol and filtered off again. Crystallization from water/ethanol/isopropanol gives the pure title compound (100 mg) containing 0.2 moles of HCl.

Anal. Calcd. for C$_7$H$_{13}$FN$_2$O$_4$, 0.2 HCl: C, 39.02; H, 6.17; N, 13.00; Found: C, 39.09; H, 6.15; N, 12.80

HCl calcd. (mole-%): 0.20 Found: 0.18

NMR(D$_2$O; Ref.: TMPS): 2.0–2.2(4H, m; H$_3$H$_4$), 4.13(1H, m; H$_5$), 4.33(1H, dd; H$_1$, J$_{F-H1}$=48 Hz, J$_{H2-H1}$=3 Hz), 5.13(1H, md; H$_2$, J$_{F-H2}$=23 Hz).

EXAMPLE III

PREPARATION OF 1,5-DIAMINO-2,2-DIFLUORO-1,5-PENTANE DICARBOXYLIC ACID (δ,δ-DIFLUORO-ε-CARBOXYLYSINE)

2,2-difluoro-4-pentene-1-ol (28)

A solution of 2,2-difluoro-4-pentenoic acid ethyl ester (32.5 g, 198 mmoles) in ethanol (100 ml) is added to a suspension of sodiumborohydride (5.7 g, 150 mmoles) in ethanol (100 ml), previously cooled to 0° C., at such a rate that the internal temperature is maintained below 10° C. The reaction mixture is kept at room temperature for 2 hours, hydrolyzed carefully with 1N H$_2$SO$_4$ and water, and diluted with dichloromethane (600 ml). The organic layer is washed twice with brine (2×250 ml), dried over sodium sulfate, and concentrated under reduced pressure (500 mm Hg, 25° C.). Distillation of the residue (15 mm, 42°–46° C.) affords pure (28) (17.05 g, 70%).

2,2-difluoro-1-benzyloxy-4-pentene (29)

To a mixture of 2,2-difluoro 4-pentene (9.8 g, 80 mmoles) and benzyl bromide (13.7 g, 80 mmoles) in dry tetrahydrofuran (100 ml), potassium t-butoxide (9.5 g, 85 mmoles) is added in portions over a period of 1 hour. The reaction mixture is kept overnight at room temperature, concentrated under reduced pressure, hydrolyzed with 1N HCl (pH approximately 2) and diluted with water and ether. Usual work-up gives 2,2-difluoro-1-benzyloxy-4-pentene as a colorless oil (16.8 g, , 99%, RF: 0.2, ethyl acetate/petroleum ether: 2/98).

2,2-difluoro-1-benzyloxy-5-hydroxypentane (30)

To a mixture of (29) (16.8 g, 79 mmoles) and sodium borohydride (901 mg, 23.7 mmoles, 20% excess) in dry tetrahydrofuran (75 ml), kept under nitrogen at room temperature, borontrifluoride-ether complex (4.07 ml, 31.6 mmoles, 20% excess) is added over a period of 25 min. After standing for 1¾ hours at room temperature, the reaction mixture is slowly hydrolyzed with water (6 ml). Addition of 3N NaOH (10 ml) is followed by careful introduction of hydrogen peroxide (10 ml, 30%) at such a rate that the internal temperature does not exceed 40° C. The temperature is then allowed to return to room temperature, and the reaction mixture is diluted with ether and brine. Usual work-up affords a mixture of isomeric alcohols (17.2 g) which is separated by chromatography on silica (ethyl acetate/petroleum ether: 15/85, RF: 0.1) to give 9.8 g (54%) of the title compound.

2,2-difluoro-1-benzyloxy-5-methoxypentane (31)

Excess methyl iodide (17 g, 120 mmoles) is added to the alcoholate previously prepared from 2,2-difluoro-1-benzyloxy-5-hydroxypentane (9.8 g, 42.6 mmoles) and potassium t-butoxide (5.6 g, 50 mmoles) in dry tetrahydrofuran (50 ml). The reaction mixture is kept at room temperature overnight, concentrated under vacuum, and the residue is deluted with water and ether. Usual extraction gives the title compound which is purified by chromatography on silica (ethyl acetate/petroleum ether: 20/80, RF: 0.9; 7.4 g, 71%).

2,2-difluoro-1-hydroxy-5-methoxypentane (32)

Trimethylsilyliodide (5.2 g, 26 mmoles) is added to a solution of 2,2-difluoro-1-benzyloxy-5-methoxypentane (6.3 g, 25.8 mmoles) in dry dichloromethane (30 ml), kept under nitrogen at room temperature. After standing for 1 hour at 25° C., the reaction mixture is treated with triethylamine (5 ml) during 1 hour, diluted with dichloromethane and washed with 1N HCl and twice with diluted brine. Bulb to bulb distillation of the crude oil obtained (4.2 g) (110°–150° C., 15 mm) gives the title compound (2.7 g, contaminated with 10% of 2,2-difluoro-1-benzyloxy-5-hydroxy pentane).

2,2-difluoro-5-methoxy-1-pentanal hydrate (33)

A solution of dry dimethylsulfoxide (3 g, 38 mmoles) in dry dichloromethane (15 ml) is slowly added to a solution of oxalyl chloride (2.4 g, 19 mmoles) in dichloromethane (15 ml), kept under nitrogen and cooled to −60° C. Stirring is continued for 15 min. at −60° C. and followed by addition of 2,2-difluoro-1-hydroxy-5-methoxypentane (2.7 g, 17.5 mmoles) in dichloromethane (15 ml). The reaction mixture is stirred for 1½ hours at −60° C., triethylamine (8.4 ml, 114 mmoles) in dichloromethane (15 ml) is slowly added, and the cooling bath is removed. The reaction mixture is hydrolyzed with brine and diluted with dichloromethane. The organic phase is then washed successively with 2N HCl containing some sodium chloride, and brine. Usual work-up affords the title compound (1.59 g, 53%) which is used for the next step without further purification.

2,2-difluoro-5-methoxy-1-pentanal oxime (34)

A mixture of 2,2-difluoro-5-methoxy-1-pentanal hydrate (1.57 g, 9.2 mmoles), hydroxylamino hydrochloride (640 mg, 9.2 mmoles), 1N NaOH (9.2 ml), and dioxane (15 ml) is kept for 1 hour at room temperature. After addition of ether and brine, usual extraction gives an oil which according to NMR is the oxime hydrate. Several evaporations with carbon tetrachloride (50° C., 60 mm Hg) afford the oxime (1.4 g) which is purified by chromatography on silica (ethyl acetate/petroleum ether: 20/80, RF: 0.53): 1.05 g (68%).

2,2-difluoro-5-methoxy-valeronitrile (35)

Thionyl chloride (809 mg, 6.8 mmoles) in ice cold dry dichloromethane (7 ml) is added to a solution of dimethylamino pyridine (903 mg, 7.4 mmoles) in dichloromethane (15 ml) kept under nitrogen and cooled at −15° C. The oxime 34 (1.04 g, 6.2 mmoles), dissolved in dichloromethane (20 ml) is added, followed by addition of dimethyl aminopyridine as a solid (903 mg, 7.4 mmoles). The reaction mixture is then allowed to rise to room temperature, kept at 25° C. for 1 hour, diluted with dichloromethane, washed with 1N HCl, and finally with water. Concentration of the organic phase, previously dried over sodium sulfate, (30° C., 100 mm Hg) affords the title compound (620 mg) which is purified by bulb to bulb distillation (50° C., 30 mm Hg): 485 mg (52%).

3-amino-4,4-difluoro-7-methoxy-1-heptene (36)

Under an atmosphere of nitrogen, 2,2-difluoro-5-methoxyvaleronitrile (4.85 mg, 3.25 mmoles), dissolved in tetrahydrofuran (5 ml), is slowly added to vinyl magnesium bromide (8 ml, 0.5M in tetrahydrofuran, 4 mmoles) previously cooled to −12° C. The reaction mixture is kept at −10° C. for ½ hour and then cooled to −40° C. A solution/suspension of sodium borohydride (133 mg, 3.5 mmoles) in methanol (14 ml) and water (0.5 ml), cooled to −40° C., is poured into the mixture, The temperature is allowed to rise to 0° C., and the mixture kept at this temperature for 10 min. The mixture is acidified with 6N HCl and concentrated under reduced pressure. The residue is dissolved in water, the aqueous solution is extracted twice to remove by-products, made alkaline with 4N NaOH, saturated with sodium chloride, and extracted again twice with ether. Usual work-up gives the title compound as a yellowish oil which is used for the next step without further purification: 420 mg (70)%.

3-phthalimido-4,4-difluoro-7-methoxy-1-heptene (37)

A mixture of 3-amino-4,4-difluoro-7-methoxy-1-heptene (420 mg, 2.3 mmoles) and N-carbetoxyphthalimide (506 mg, 2.3 mmoles) in benzene (9 ml) is kept at 25° C. overnight. After concentration under reduced pressure, the residue is dissolved in dichloromethane (5 ml) and treated with triethylamine (0.7 ml) for 4½ hours. After addition of dichloromethane, the solution is washed with 1N HCl and water. Usual work-up affords an oil (610 mg) which is purified by chromatography on silica (ethyl acetate/petroleum ether: 20/80 RF: 0.4): 440 mg (62%).

3-phthalimido-4,4-difluoro-7-hydroxy-1-heptene (38)

Under an atmosphere of nitrogen, a mixture of 3-phthalimido-4,4-difluoro-7-methoxy-1-heptene (440 mg, 1.43 mmoles) and trimethylsilyliodide (400 mg, 2 mmoles) in dry dichloromethane (10 ml) is heated overnight under reflux. 1N HCl (10 ml) is added to the reaction mixture which is kept under vigorous stirring for ½ hour. The organic layer is separated, washed successively with water, sodium bisulfite solution, and water, and is dried over sodium sulfate. 3-phthalimido-4,4-difluoro-7-hydroxy-1-heptene is obtained as a solid: 3.85 mg (91%).

4,4-difluoro-5-phthalimido-6-hepten-1-al (39)

The procedure used is identical with the one described for the preparation of 2,2-difluoro-5-methoxy-1-pentanal hydrate. Each component was dissolved in 3 ml of dry dichloromethane, and the amounts used were the following: oxalyl chloride: 191 mg (1.5 moles), dimethylsulfoxide: 235 mg (3 mmoles), alcohol: 380 mg (1.3 mmoles), triethylamine: 909 mg (9 mmoles). Usual work-up gave the aldehyde as a solid (355 mg), which was recrystallized from dichloromethane/pentane (274 mg, 72%, RF: 0.74 (ethyl acetate/petroleum ether: 30/70).

3-hydroxy-6,6-difluoro-7-phthalimido-1,8-nonadiene (40)

Under an atmosphere of nitrogen, vinyl magnesium bromide (1 ml of 1M solution in tetrahydrofuran) is added to 4,4-difluoro-5-phthalimido-6-hepten-1-al (274 mg, 0.93 mmoles), dissolved in dry tetrahydrofuran (5 ml) previously cooled to −70° C. The temperature is allowed to rise to −5° C., and the reaction mixture is quenched with a saturated solution of ammonium chloride, diluted with ether, and the layers are separated. The alcohol obtained as an oil (300 mg) is purified by chromatography on silica (ethyl acetate/petroleum ether: 70/30, RF: 0.61): 148 mg (49%).

3,7-diphthalimido-6,6-difluoro-1,8-nonadiene (41)

A mixture of 3-hydroxy-6,6-difluoro-7-phthalimido-1,8-nonadiene (148 mg, 0.46 mmoles), phthalimide (73.5 mg, 0.5 mmoles), triphenylphosphine (131.5 mg, 0.5 mmoles) and diethyl azodicarboxylate (73 1, 0.6 mmoles) in tetrahydrofuran (5 ml) is kept under nitrogen at 25° C. for 20 hours. After concentration under reduced pressure, the title compound is obtained after purification by chromatography on silica (dichloromethane, RF: 0.43): 95 mg (46%).

3,7-di-t-butoxycarbonylamino-6,6-difluoro-1,8-nonadiene (43)

A mixture of 3,7-diphthalimido-6,6-difluoro-1,8-nonadiene (95 mg, 0.21 mmoles), hydrazine hydrate (0.43 ml of a 1M solution in ethanol) in ethanol (0.3 ml), and tetrahydrofuran (0.1 ml) is kept for 2 days at 25° C. and then heated for 1 hour at 80° C. 6N HCl (1 ml) is added to the mixture, and heating is continued for 2 hours. After cooling, the reaction mixture is filtered and concentrated under vacuum. The residue, di-t-butyldicarbonate (109 mg, 0.5 mmoles), triethylamine (60 mg, 0.6 mmoles), water (0.2 ml), and tetrahydrofuran (0.6 ml) are kept under magnetic stirring overnight at room temperature. After concentration under reduced pressure, usual extraction with ether and water gives the title compound (85 mg) which is purified by chromatography on silica (ethyl acetate/petroleum ether: 15/85, RF: 053): 40 mg (50%).

1,5-di-t-butoxycarbonylamino-2,2-difluoro-1,5-pentanedicarboxylic acid (44)

($N^\alpha,N^\epsilon$-di-tert-butoxycarbonyl-δ,δ-difluoro-ε-carboxylysine)

3,7-di-t-butoxycarbonylamino-6,6-difluoro-1,8-nonadiene (40 mg, 0.1 mmoles), dissolved in acetic acid (1 ml), is added to a well stirred solution of potassium permanganate (95 mg, 0.6 mmoles) in water (5 ml). After 20 hours at room temperature, the reaction mixture is saturated with sodium chloride, discolored with sodium bisulfite, and extracted with ether. After drying and concentration of the organic phase, the residue (50 mg) is dissolved in ether, washed with sodium bicarbonate, and the aqueous phase is acidified to pt 2–3 with 1N HCl. After saturation with sodium chloride, the mixture is extracted with ether. Usual work-up gives the diacid (34 mg, 80%) which is used for the next step without further purification.

1,5-diamino-2,2-difluoro-1,5-pentanedicarboxylic acid, dihydrochloride (2)

(δ,δ-difluoro-ε-carboxylysine)

2,6-di-t-butoxycarbonylamino-3,3-difluoro-1,7-heptanedioic acid (34 mg, 0.08 mmoles) is dissolved in dry ether saturated with HCl gas. After standing overnight and filtration, the title compound is obtained as a white solid (9 mg, 38%, RF: 0.4 (ethanol, conc. ammonia: 70/30, RF: 0.1 (butanol/acetic acid/water: 4/2/2)

EXAMPLE IV

PREPARATION OF δ-FLUORO-ε-CARBOXYLYSINE, METHYL ESTER 5-fluoro-2,6-diaminopimelic acid, methyl ester, dihydrochloride 5-fluoro-2,6-di-tert-butoxycarbonylamino-7-octenoic acid (600 mg, 1.54 mmoles) is dissolved in ether (5 mL) and heated with an ether solution of diazomethane until the color of the solution stays yellow. After 10 min at room temperature, evaporation yields an oil (620 mg) which is dissolved in acetic acid (6 mL) and water (48 mL). Potassium permanganate (732 mg, 4.62 mmoles) is added, and the mixture is stirred at room temperature overnight. After addition of sodium bisulfite and saturation with sodium chloride, extraction (ether, twice) and evaporation yields $N^\alpha,N^\epsilon$-di-t-butoxycarbonyl-ε-carboxylysine methyl ester as a colorless oil: 640 mg. This is dissolved in ether (30 mL), saturated with HCl gas and stirred overnight at room temperature to give the title compound as hygroscopic white crystals (360 mg).

EXAMPLE V

PREPARATION OF δ-FLUORO-ε-CARBOXYLYSYL-L-ALANYL-L-ALANINE

Preparation of L-alanyl-L-alanine tert-butyl ester, acetate (51)

In a 2 L three-necked flask, L-alanine (54.0 g) is dissolved in 2N NaOH (305 mL) and cooled to 0° C. in an ice-bath. To this solution, carbobenzoxychloride (90 mL) and 2N NaOH (305 mL) are simultaneously added dropwise so that the reaction temperature does not exceed 5° C. After complete addition, the ice-bath is removed and the reaction mixture stirred for 2 hours at room temperature. Diethylether is added (100 mL) and the organic phase is separated. The aqueous phase is washed once more with Et$_2$O (100 mL), and acidified to pH 1 with HCl (2N). Ethylacetate (150 mL) is added, and the organic phase is separated. The aqueous phase is extracted with AcOEt (3×150 mL), and the combined organic phases are washed with H$_2$O (3×100 mL). After drying (MgSO$_4$), the solvent is removed (20 Torr/30° C.) to leave a colorless oil, which crystallizes upon standing (110 g). Recrystallization (AcOEt/hexane) affords 100 mg (73%) of benzyloxycarbonyl-L-alanine, m.p. 85° C.; $[\alpha]^{23} = -14.3$ (c=2 in AcOH).

In a 2 L one-neck flask, L-alanine (6.23 g) is stirred for 4 days with 1.1 L of t-butylacetate at room temperature and perchloric acid (70%, 6.65 mL, 7.7 g). The mixture is concentrated to ¼ of its original volume, and the residue extracted at 0°–5° C. with 0.5N HCl (4×60 mL). The aqueous phase is immediately neutralized with KHCO$_3$ (solid). The pH is adjusted to 13 with 4N NaOH, and the solution extracted with Et$_2$O (4×100 mL). The combined organic layers are washed with bicarbonate solution (2×50 mL), dried (MgSO$_4$), and evaporated. The oily residue is dissolved in 10 mL of Et$_2$O (anh.) and treated with HCl:Et$_2$O under cooling. The precipitated salt is filtered and dried to yield 4 g of L-alanine-t-butyl ester hydrochloride having a m.p. 167° C.; [α]$^{20}$= +177 (c=2 in EtOH).

To a stirred solution of the benzyloxycarbonyl-L-alanine prepared above (5.83 g, 25 mmoles) in CH$_2$Cl$_2$, a solution of 1-hydroxybenzotriazol-hydrate (3.85 g, 25 mmoles) in 20 mL of tetrahydrofuran is added. After cooling to 0° C. (ice-bath), dicyclohexylcarbodiimide (5.67 g, 27.5 mmoles) is added in one portion. The icebath is removed after 1 hour, and the mixture again cooled to 0° C. Stirring is continued after addition of N-methylmorpholine (2.8 mL, 25 mmoles) for ½ hour at 0° C. and 2 hours at room temperature. The precipitated dicyclohexylurea is removed by filtration through a sintered glass filter, 50 mL of CH$_2$Cl$_2$ added, and the solution is extracted with a saturated KHCO$_3$ solution, and 1N HCl (ca. 3×50 mL, pH control). After washing with brine and H$_2$O (ca. 2×25 mL) the solution is dried (MgSO$_4$), and evaporated to afford a colorless oil, which is dissolved in anhydrous acetonitrile and stored overnight at −18° C. The precipitated dicyclohexylurea is removed by filtration, and the solution is evaporated to dryness to yield (Z-)-L-alanyl-L-alanine-tert-butyl ester as a colorless oil, 8.12 g (93%).

This compound (7.0 g, 20 mmoles) is dissolved in i-Propanol (100 mL) and glacial acetic acid (5 mL). Pd/C (1.0 g Fluka) is added under N$_2$, and the mixture is stirred for 20 hours under H$_2$ (1 atm., 3 times renewed). The catalyst is filtered (celite), and evaporation of the solvents yields a colorless oil, which crystallizes upon addition of anhydrous Et$_2$O. The resulting crystals are filtered and dried to yield (hygroscopic) L-alanyl-L-alanine-tert-butyl ester, acetate (yield 4.6 g-83%).

δ-Fluoro-ε-vinyllysyl-L-alanyl-L-alanine, t-butyl ester (52)

The compound 2,6-di-tert-butoxycarbonylamino-5-fluoro-7-octenoic acid, 26, prepared as in Example II above (2.613 g, 6.7 mmoles) is dissolved in dichloromethane and 1-hydroxybenzotriazole monohydrate (1.04 g, 6.7 mmoles) is added thereto. The suspension is stirred at room temperature for 15 minutes and then cooled to 0° C. Dicyclohexylcarbodiimide (1.52 g, 7.37 moles) is added, and the mixture is stirred for 1 hour at 0° C. and for 2 hours at room temperature.

In the meantime, L-alanyl-L-alanine-tert-butyl ester, acetate, prepared above (51, 2.77 g, 10 mmoles) is suspended in tetrahydrofuran (10 mL), and 2N NaOH (6 mL) is added slowly. After 20 minutes, CH$_2$Cl$_2$ (25 mL) is added, the organic phase is separated, dried (Na$_2$SO$_4$) and evaporated to yield the free dipeptide-ester as an oil (2.1 g). This oil, 1.6 g (7.4 mmoles) is dissolved in CH$_2$Cl$_2$ (5 mL) and added to the cold (0° C.) reaction mixture described above. After stirring overnight, the mixture is filtered, washed with potassium bicarbonate (3×30 mL), KHSO$_4$ (3×30 mL), and water (20 mL). Drying (MgSO$_4$) and evaporation yields a slightly yellow oil, which is dissolved in CCl$_4$ (50 mL) and kept at −18° C. for 2 hours. Filtration and evaporation gives 52 as a slightly yellow oil: 3.1 g (79%).

TLC: AcOEt/AcOH (1-2 drops): R$_f$ about 0.8, 1 spot.
AcOEt/pentane (1:1): R$_f$ about 0.2, 1 spot.

δ-Fluoro-ε-carboxylysyl-L-alanyl-L-alanine, t-butyl ester (53)

A solution of 52 above (2.9 g, 4.93 mmoles) in acetic acid (20 mL) is added to a solution of potassium permanganate (2.3 g, 3 equiv.) in water (100 mL) with ice cooling. After stirring for 14 hours at room temperature, MnO$_2$ is dissolved by addition of conc. sodium bisulfite solution. Extraction with ethyl acetate and evaporation gives a residue which is dissolved in ether. Re-acidification with KHSO$_4$ solution and extraction with ether, drying (Na$_2$SO$_4$) and evaporation yields the corresponding N$^α$,N$^ε$-di-t-butoxycarbonyl-δ-fluoro-Δ-carboxylysyl-L-alanyl-L-alanine t-butyl ester, 53 as a white foam: 1.80 g (60%). Removal of the amino protecting groups from 53, is achieved by dissolving (1.809) in ether saturated with HCl gas and stirred at room temperature for 4 days. The title compound is obtained as a white, somewhat hygroscopic solid: 1.10 g (88%).

EXAMPLE VI

PREPARATION OF
δ-FLUORO-ε-CARBOXYLYSYL-L-ALANINE

N$^α$,N$^ε$-di-t-butoxycarbonyl-δ-fluoro-ε-vinyllysyl-L-alanine t-butyl ester (52)

The compound 5-fluoro-2,6-di-tert-butoxycarbonylamino-7-octenoic acid, 26, prepared as in Example II above (636 mg, 1.63 mmoles), 1-hydroxybenzotriazole monohydrate (250 mg) and dry dichloromethane (30 mL) are stirred at room temperature for 15 minutes. After cooling to 0° C., dicyclohexylcarbodiimide (370 mg) is added and stirring is continued for 1 hour at 0° C. and for 2 hours at room temperature. After cooling to 0° C. again, L-alanine-tert-butylester, hydrochloride (296 mg) is added, followed by N-methylmorpholine (330 mg). The mixture is stirred for 1 hour at 0° C., then at room temperature overnight. Filtration, washing (NaHCO$_3$, NaHSO$_4$, water), drying (Na$_2$SO$_4$) and evaporation yields an oil. This oil is dissolved in dichloromethane, filtered and evaporated. This last procedure is repeated several times to completely remove the DCU, leaving the title compound as an oil, 800 mg (95%).

N$^α$,N$^ε$-di-t-butoxycarbonyl-δ-fluoro-ε-carboxylysyl-L-alanine t-butyl ester (53)

The N$^α$,N$^ε$-di-t-butoxycarbonyl-δ-fluoro-ε-vinylysyl-L-alanine t-butyl ester prepared above (800 mg, 1.53 mmoles), dissolved in glacial acetic acid (6 mL), is added to a solution of KMnO$_4$ (730 mg) in water (30 mL) and acetone (5 mL) with ice cooling. After stirring at room temperature overnight, sodium bisulfite is added to dissolve the MnO$_2$, the solution is saturated with NaCl, and extracted with ether. Drying and evaporation gives an oil which is dissolved in ether. Extraction with aq. NaHCO$_3$ (twice), acidification (HCl 1N), re-extraction (ether) and usual work-up gives the above compound as a white foam: 511 mg (62%).

δ-Fluoro-ε-carboxylysyl-L-alanine (3)

The N$^α$,N$^ε$-di-t-butoxycarbonyl-δ-fluoro-ε-carboxylysyl-L-alanine t-butyl ester prepared above (511 mg) is dissolved in ether saturated with HCl gas, and the mixture is stirred at room temperature for 4 days. The precipitate is collected and dissolved in 1N HCl. Evaporation gives a white foam which is dried carefully and is dissolved in ethanol. Upon addition of excess propylene oxide, the title compound crystallizes with 0.75 mmoles of HCl and 0.75 mmoles of water.

Anal. Calcd. for $C_{10}H_{18}FN_3O_5$, $\frac{3}{4}HCl$, $\frac{3}{4}H_2O$: C, 38.04; H, 6.07; N, 13.31; Found: C, 38.34; H, 6.23; N, 13.02

EXAMPLE VII

GROWTH OF BACTERIA AND ISOLATION OF DAP-EPIMERASE (EC 5.1.1.7) (DAP-EPIMERASE)

Strains were inoculated into Nutrient bath (5 ml) and grown up overnight (16 hours) at 37° C. Small amounts of cells were obtained in shake flask cultures (50 ml–1000 ml) obtained by innoculating Igarashi medium (Igarashi et al., 1979), with 2% of the starter culture. Cells were harvested at late-log (OD 540 nm 0,7–0,8) and rinsed before storage at −20° C. Larger amounts of cells were obtained using an overnight culture (Igarashi medium) of 2,5 l as innoculum for 80 l of Igarashi medium in a Biolaffite Fermenter. Cells were harvested in late-log (OD 540 nm 2.0) using a filtration system for cell concentration (40 fold) followed by centrifugation.

Cells from E. Coli (PR7), usually in batches of 40 g, were suspended in 100 ml buffer A (20 mM potassium phosphate 1 mM EDTA, 1 mM DTT, pH 7.0) by using the Ultraturrax apparatus (10 min). Passage through the French press (20,000 lbs/sq ins) and centrifugation 30,000 xg for 20 min gave the S30 crude extract. The supernatent was fractionated by adding solid ammonium sulfate to 30%, centrifugation was followed by further ammonium sulfate to 45%. The precipitated protein was dissolved in buffer to give a final volume of 10 ml which was dialysed overnight against 2,000 ml of buffer A.

The dialysed crude enzyme preparation was applied to a DEAE-cellulose column (2.3×49 cms) DES52, equilibrated with buffer A. The column was washed with 250 ml of buffer A and eluted with a linear gradient formed by adding 250 ml of buffer A containing 0,22M KCl to 250 ml of buffer A. The flow rate was 25 ml/hr and 10 ml fractions were collected. DAP-epimerase eluted near the end of the gradient at approximately 0,20M KCl. Pooled fractions containing DAPepimerase activity were dialysed overnight against 2,000 ml buffer A. Enzyme was concentrated by applying the dialysate to a smal DES52 column (0.9×10 cms), rinsing with 50 ml of buffer A and eluting with buffer A containing 0,50M KCl. The flow-rate was 20 ml/hr and 2,5 ml fractions were collected. Enzyme activity eluted immediately and pooled fractions were dialized against 1,000 ml buffer A.

Enzyme, concentrated in this fashion, was stable at 4° C. for many months but lost activity upon freezing.

A final purification step was obtained by applying the concentrated dialysed enzyme to a dye ligand column (1,4×5 cms), Matrix green A, rinsing with 50 ml buffer A and then eluting with 50 ml of buffer A containing 1,2M HCl collecting 5 ml fractions. Pooled fractions were dialysed and concentrated on a small DE52 as described above.

Enzyme activity

DAP-epimerase activity was routinely measured at 25° C. Reaction mixtures contained 0.1M Tris HCl (pH 7,8), 1 mH EDTA, 1 mM DTT and 0,5 C of [G-$^3$H]DAP in a total volume of 0.10 ml. After incubation for 40 min, reaction mixtures were quenched with 0.5 ml of 10% TCA and applied to 1 ml of AG50×4 ion-exchange resin (H' form) contained in a column (about 0.4×2 cms) fashioned from a blue pipette cone. The column was washed with 3×0.5 ml of water and the combined eluants counted for radioactivity.

Enzyme inhibition studies

In vitro DAP-epimerase, purified as described above, was incubated at 25° C. with various concentrations of δ-fluoro-ε-carboxylysine (usually 0, 10, 20, 40, 80 and 100M) as described in the enzyme assay above. In cases where aliquots were removed and deluted 50-fold with the assay medium, no inhibition was observed.

In vivo-*Aerobacter aerogenes* grown overnight in Roche medium (Atherton et al., 1979) was diluted 50 fold into fresh Roche medium and growth monitored by turbidity measurement at 540 mm. After ensuring that growth was in log-phase, bacterial cultures were divided for control and for treatment with either δ-fluoro-ε-carboxylysyl-L-alanyl-L-alanine or δ-fluoro-ε-carboxylysyl-L-alanine essentially as described by Atherton et al. (1979). After time periods of 5, 10, 15, 20, 30 min aliquots were removed and poured onto ice. Following centrifugation at 30,000 g, 30 min, cells were washed with buffer A and stored at −20° C.

For enzyme activity determinations, cells were sonicated (4×30 sec) in buffer A, centrifuged and crude extracts assayed for DAP-epimerase activity as described above.

TABLE 1

| PURIFICATION OF DIAMINOPIMELIC ACID EPIMERASE [EC 5.1.1.7] | | | | | |
|---|---|---|---|---|---|
| Fraction | Volume (ml) | Protein (mg/ml) | Specific Activity (dpm/μg) | Purification (fold) | Yield (%) |
| S30 Extract | 185 | 11,7 | 4,900 | 1 | 100 |
| Ammonium Sulfate (30–45%) | 13,3 | 36,4 | 13,800 | 2,8 | 63 |
| DE52-Column (gradiant) | 89 | 0,57 | 67,700 | 13,8 | 33 |
| DE52-Column (concentration) | 8 | 4,94 | 70,200 | 14,3 | 26 |
| Dye ligand (Matrix) | 16,3 | 0,116 | 399,000 | 82 | 7,1 |
| DE52-Column (concentration) | 3,7 | 0,39 | 512,000 | 105 | 7,0 |

| Inhibition of *Escherichia coli* DAP-epimerase (E.C. 5.1.1.7) | | |
|---|---|---|
| Inhibitor | $K_i^+$ | $IC_{50}$ (μM) |
| δ-fluoro-ε-carboxylysine | 7,7 μM | $1,35 \times 10^{-6}$ |
| δ-chloro-ε-carboxylysine | 0,5 μM | N.D. |

-continued

| Inhibition of Escherichia coli DAP-epimerase (E.C. 5.1.1.7) | | |
|---|---|---|
| Inhibitor | $K_i^+$ | $IC_{50}$ ($\mu M$) |
| δ,δ-difluoro-ε-carboxylysine | N.D. | $50 \times 10^{-6}$ |

*Values determined by Dixon plots (Ref. Dixon, M., 1972).

δ-fluoro-ε-carboxylysine was tested similarly against DAP-epimerase (EC 5.1.1.7) partially purified from [Aerobacter aerogenes, Serratia marcescens, and *Pseudomonas aerogenosa* (used as test organisms-see Example VIII) and gave Ki's ranging from 1,0 μM to 5,4 μM.

REFERENCES

Atherton, F. R., Hall, M. J., Hassall, C. H., Lambert, P. W. and Ringrose, P. S. (1979). Antimicrob. Agents Chemother.: 15, 677.

Igarashi, K., Kashiwagi, K., Kishida, K., Watanabe, Y., Kogo, A. and Hirosa, S. (1979) Env. J. Biochem. 93, 345.

Dixon, M. (1972). Biochem. J. 129, 197.

EXAMPLE VIII

The following example illustrates the in vitro activity of the compounds of this invention against a variety of pathogenic organisms.

| Organism | δ-fluoro-ε-carboxy lysylalanine MIC (μg/ml)* | δ-fluoro-ε-carboxy-lysylalanylalanine MIC (μg/ml)* | Inhibition of** DAP-epimerase |
|---|---|---|---|
| E. coli (PR7) | 12,5 | 12,5 | 7,7 μM |
| A. aerogenes (62.1) | 6 | 12,5 | 1,2 μM |
| P. aerogerosa (ATCC 25619) | 0,80 | 100 | 5,4 μM |
| S. marcescens (ATCC 8100) | 0,20 | 0,20 | 1,0 μM |

*Serial dilutions in plates as described by Atherton et al. (1979).
**DAP-epimerase was partially purified from each organism as described (Example VII) through to the first DE52 column except that with Aerobacter aerogenes the ammonium sulfate fraction 45-75% was used.

EXAMPLE IX

In vivo studies

Groups of 3 fasted CFW mice (20 g±2) were dosed subcutaneously with 20, 50 or 100 mg/kg or orally with 50 or 100 mg/kg of δ-fluoro-ε-carboxylysyl-L-alanyl-L-alanine. At intervals of from 10 min to 210 min, after dosing animals were anesthetised with ether, and heparinized blood samples obtained by eye-puncture. Samples were kept on ice and the plasma removed. After dilution (1:1) with saline, aliquots were assayed for δ-fluoro-ε-carboxylysyl-L-alanyl-alanine by bioassay.

Bioassay

The antibacterial activity of δ-fluoro-ε-carboxylysyl-L-alanyl-alanine was determined by plate assay on "Roche" agar medium (adjusted to pH 6,5-see Atherton et al. (1979) using *Aerobacter aerogenes* as the test strain. Standard solutions of δ-fluoro-ε-carboxylysyl-L-alanyl-alanine were prepared by suitable dilutions in water (from the same solution used for injection) and 0,4 μg to 7,0 μg were applied to sterile discs (9 mm dia.) concomittently with serum samples. After overnight incubation at 37° C., zones of inhibition were measured across two diameters. A standard plot of zone diameter vs log. concentration of standards was prepared. The average serum concentration of δ-fluoro-ε-carboxylysyl-L-alanyl-alanine from 3 mice was taken from this standard plot. Control serum had no activity and 50% serum had no effect on the standard plot.

| Dose of δ-fluoro-ε-carboxy-lysyl-L-alanyl-L-alanine (mg/kg) | Maximum Serum Level (g/ml) | Serum half-life (min) |
|---|---|---|
| 20 | 29 ± 4 | |
| 50 S.C. | 50 | 72 |
| 100 | 96 ± 12 | |
| 50 P.O. | 27 | 64 |
| 100 | 31 | |

Thus, the compound δ-fluoro-ε-carboxylysyl-L-alanyl-L-alanine provides serum levels that are consistently above the minimum inhibition concentrations of certain infectious microorganisms, e.g. *Serratia marcescens*.

EXAMPLE X

PREPARATION OF A CAPSULE FORMULATION

An illustrative composition for hard gelatin capsules is as follows:

| | Per tablet |
|---|---|
| (a) δ-fluoro-ε-carboxylysyl-L-alanyl-L-alanine | 200 mg |
| (b) Talc | 35 mg |

The formulation is prepared by passing the dry powder of both (a) and (b) above through a fine mesh screen and mixing them well. The powder is filled into No. 0 hard gelatin shell capsules at a net fi311 of 235 mg per capsule.

In a similar fashion, a soft gelatin capsule can be prepared in which the talc is omitted. The dry hydrochloride salt can be directly filled as a granulation, slug or compresed tablet directly into a rotary dye or plate mold in which the soft gelatin capsule is formed. Lubricants and binding agents can be added, as necessary.

EXAMPLE XI

PREPARATION OF A TABLET FORMULATION

An illustrative composition for tablets is as follows:

| | Per tablet |
|---|---|
| (a) δ-fluoro-ε-carboxylysyl-L-alanyl-L-alanine | 200 mg |
| (b) Wheat starch | 15 mg |
| (c) Lactose | 83.5 mg |
| (d) Magnesium stearate | 1.5 mg |

The granulation obtained upon mixing lactose, starch and/or granulated starch paste is dried, screened and mixed with the active ingredient and magnesium stearate. The mixture is compressed into tablets each weighing 300 mg.

We claim:

1. A 2,6-diamino-3-haloheptanedioic acid derivative having the formula

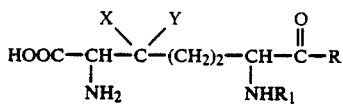

wherein
- R is hydroxy, $(C_1-C_4)$alkoxy or an amino acid, dipeptide or tripeptide residue said amino acid, dipeptide or tripeptide residue being composed of the amino acid selected from the group consisting of glycine and the L-isomers of alanine, methionine, valine, leucine and isoleucine;
- $R_1$ is hydrogen or an amino acid, dipeptide or tripeptide residue dipeptide or tripeptide residue being composed of the amino acid selected from the group consisting of glycine and the L-isomers of alanine, methionine, valine, leucine and isolencine, and there simple amides, with the proviso that when $R_1$ is an amino acid, dipeptide or tripeptide residue, then R must be hydroxy, and with the further proviso that when R is an amino acid, dipeptide or tripeptide residue, then $R_1$ must be hydrogen;
- X and Y are independently hydrogen, fluorine or chlorine, with the proviso that X and Y cannot both be hydrogen; and the pharmaceutically acceptable salts or optical isomers thereof.

2. A compound according to claim 1 wherein X is fluorine and Y is hydrogen.

3. A compound according to claim 1 wherein X is chlorine and Y is hydrogen.

4. A compound according to claim 1 wherein X and Y are each fluorine.

5. A compound according to claim 1 wherein R is an amino acid residue and $R_1$ is hydrogen.

6. A compound according to claim 1 wherein R is a dipeptide residue and $R_1$ is hydrogen.

7. A compound according to claim 1 wherein R is a tripeptide residue and $R_1$ is hydrogen.

8. A compound according to claim 1 wherein R is hydroxy and $R_1$ is hydrogen.

9. A compound according to claim 1 which is 2,6-diamino-3-chloroheptanedioic acid or its pharmaceutically acceptable salts.

10. A compound according to claim 1 which is 2,6-diamino-3-fluoroheptanedioic acid or its pharmaceutically acceptable salts.

11. A compound according to claim 1 which is 2,6-diamino-3,3-difluoroheptanedioic acid or its pharmaceutically acceptable salts.

12. A compound according to claim 1 which is δ-fluoro-ε-carboxylysyl-L-alanine or its pharmaceutically acceptable salts.

13. A compound according to claim 1 which is δ-fluoro-ε-carboxylysyl-L-alanyl-L-alanine or its pharmaceutically acceptable salts.

14. An antibacterial composition comprising an effective amount of a compound of claim 1, or a pharmaceutical acceptable salt thereof, in combination with a pharmaceutically acceptable carrier.

15. An antibacterial composition comprising an effective amount of a compound of claim 2, or a pharmaceutical acceptable salt thereof, in combination with a pharmaceutically acceptable carrier.

16. An antibacterial composition comprising an effective amount of a compound of claim 6, or a pharmaceutical acceptable salt thereof, in combination with a pharmaceutically acceptable carrier.

* * * * *

UNITED STATES PATENT AND TRADEMARK OFFICE
CERTIFICATE OF CORRECTION

PATENT NO. : 4,730,006
DATED : March 8, 1988
INVENTOR(S) : Ekkehard H. Bohme, Fritz Gerhart, William Higgins

It is certified that error appears in the above-identified patent and that said Letters Patent are hereby corrected as shown below:

At column 5, line 30, structure 2, the patent reads

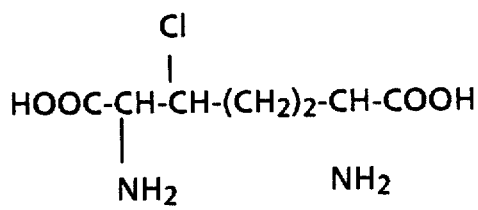

and should read

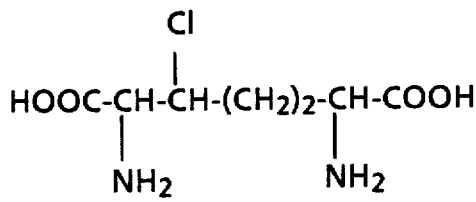

At column 7, structure 23, the patent reads

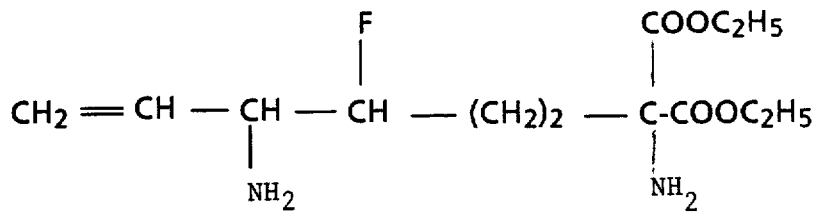

UNITED STATES PATENT AND TRADEMARK OFFICE
CERTIFICATE OF CORRECTION

PATENT NO. : 4,730,006
DATED : March 8, 1988
INVENTOR(S) : Ekkehard H. Bohme, Fritz Gerhart, William Higgins It is certified that error appears in the above-identified patent and that said Letters Patent are hereby corrected as shown below:

and should read

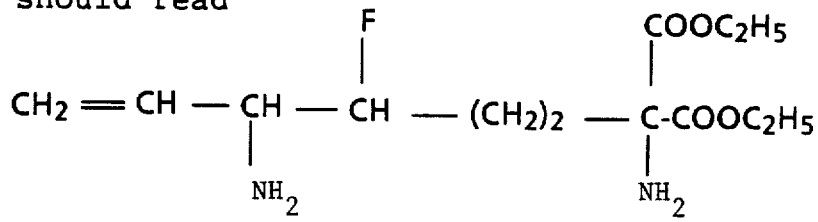

At column 8, structure 22, the patent reads

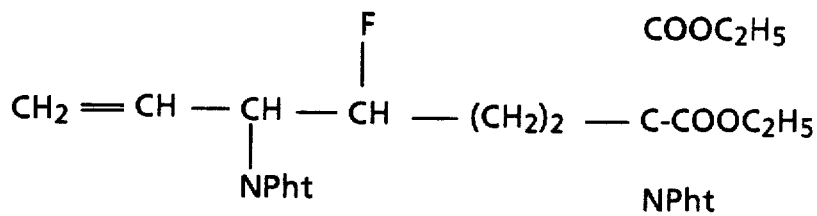

and should read

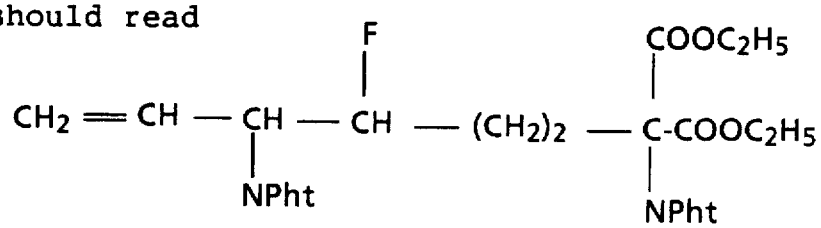

as found in the specification at page 15, line 10, structure 22.

UNITED STATES PATENT AND TRADEMARK OFFICE
CERTIFICATE OF CORRECTION

PATENT NO. : 4,730,006

DATED : March 8, 1988

INVENTOR(S) : Ekkehard H. Bohme, Fritz Gerhart, William Higgins

It is certified that error appears in the above-identified patent and that said Letters Patent are hereby corrected as shown below:

At column 9, structure 36, the patent reads

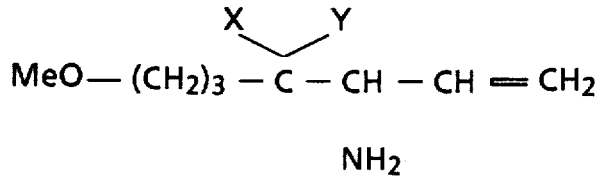

and should read

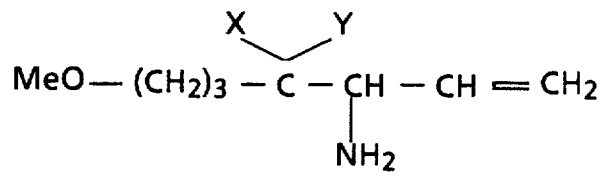

At column 27, line 9, the patent reads "the residue is deluted with water" and should read --the residue is diluted with water--.

At column 29, line 64, the patent reads "is acidified to pt 2-3 with" and should read --is acidified to pH 2-3 with--.

At column 32, lines 13 and 14, the patent reads "-δ-fluoro-Δ-carboxylysyl" and should read -- -δ-fluoro-ε-carboxylysyl --

UNITED STATES PATENT AND TRADEMARK OFFICE
CERTIFICATE OF CORRECTION

PATENT NO. : 4,730,006

DATED : March 8, 1988

INVENTOR(S) : Ekkehard H. Bohme, Fritz Gerhart, William Higgins

It is certified that error appears in the above-identified patent and that said Letters Patent are hereby corrected as shown below:

At column 36, line 39, the patent reads "net fi3ll of" and should read -- net fill of --.

At column 37, lines 15 and 16, claim 1, the patent reads "acid, dipeptide or tripeptide residue dipeptide or tripeptide residue being" and should read --acid, dipeptide or tripeptide residue being--.

Signed and Sealed this

Twenty-seventh Day of September, 1988

Attest:

DONALD J. QUIGG

Attesting Officer

Commissioner of Patents and Trademarks